(12) United States Patent
Fine et al.

(10) Patent No.: US 11,134,901 B2
(45) Date of Patent: *Oct. 5, 2021

(54) METHOD AND APPARATUS FOR OPTICALLY MEASURING BLOOD PRESSURE

(71) Applicant: ELFI-TECH LTD., Rehovot (IL)

(72) Inventors: Ilya Fine, Rehovot (IL); Alexander Kaminsky, Rehovot (IL)

(73) Assignee: ELFI-TECH LTD., Rehovot (IL)

( * ) Notice: Subject to any disclaimer, the term of this patent is extended or adjusted under 35 U.S.C. 154(b) by 684 days.

This patent is subject to a terminal disclaimer.

(21) Appl. No.: 15/938,533

(22) Filed: Mar. 28, 2018

(65) Prior Publication Data

US 2018/0310891 A1     Nov. 1, 2018

Related U.S. Application Data

(63) Continuation of application No. PCT/IB2017/053339, filed on Jun. 7, 2017, and a
(Continued)

(51) Int. Cl.
*A61B 5/00*     (2006.01)
*A61B 5/022*     (2006.01)
(Continued)

(52) U.S. Cl.
CPC .......... *A61B 5/7278* (2013.01); *A61B 5/0261* (2013.01); *A61B 5/02141* (2013.01);
(Continued)

(58) Field of Classification Search
CPC ... A61B 5/0261; A61B 5/6826; A61B 5/7278; A61B 5/02141; A61B 5/02241; A61B 5/6838; A61B 5/02422
See application file for complete search history.

(56) References Cited

U.S. PATENT DOCUMENTS

| 5,145,500 A | 9/1992 | Nolen, Jr. |
| 5,651,616 A | 7/1997 | Hustak et al. |

(Continued)

FOREIGN PATENT DOCUMENTS

EP     0537383 A1     4/1993

OTHER PUBLICATIONS

International Search Report for PCT/IL2017/051139 dated Apr. 19, 2018.
(Continued)

*Primary Examiner* — Bo Joseph Peng
(74) *Attorney, Agent, or Firm* — Momentum IP Group; Marc Van Dyke

(57) ABSTRACT

Methods and systems of optically measuring systolic and/or diastolic blood pressure of a mammal having biological tissue are disclosed herein. In some embodiments, the system comprises an optical blood motion sensor, a gas-sealable inflatable cushion having a flexible and transparent (FOT) barrier section, and an optical blood motion sensor comprising a laser. When pressure (e.g. at least systolic pressure) illuminates the tissue, laser light may pass en route to the tissue through the FOT sealing barrier section of the gas-sealable inflatable cushion as well as cushion interior. In some embodiments, a rigid restrictor comprising an optically transparent section is provided, and laser light also passes through the optically transparent section of the rigid restrictor en route to the biological tissue.

20 Claims, 38 Drawing Sheets

Related U.S. Application Data continuation-in-part of application No. 15/474,963, filed on Mar. 30, 2017, now abandoned.

(60) Provisional application No. 62/407,429, filed on Oct. 12, 2016, provisional application No. 62/315,010, filed on Mar. 30, 2016.

(51) Int. Cl.
*A61B 5/026* (2006.01)
*A61B 5/021* (2006.01)
*A61B 5/024* (2006.01)
*A61B 5/02* (2006.01)

(52) U.S. Cl.
CPC ...... *A61B 5/02241* (2013.01); *A61B 5/02422* (2013.01); *A61B 5/6826* (2013.01); *A61B 5/6838* (2013.01); *A61B 5/02* (2013.01); *A61B 5/026* (2013.01)

(56) References Cited

U.S. PATENT DOCUMENTS

| | | | |
|---|---|---|---|
| 5,651,753 A | 7/1997 | Wilkinson | |
| 5,651,782 A | 7/1997 | Simon et al. | |
| 6,172,743 B1* | 1/2001 | Kley | A61B 5/14532 356/39 |
| 6,178,342 B1* | 1/2001 | Borgos | A61B 5/02007 600/322 |
| 6,319,205 B1* | 11/2001 | Goor | A61B 5/02007 600/481 |
| 6,475,153 B1* | 11/2002 | Khair | A61B 5/02007 600/485 |
| 6,669,648 B1 | 12/2003 | Fortin et al. | |
| 6,801,798 B2 | 10/2004 | Geddes et al. | |
| 7,341,560 B2 | 3/2008 | Henderson et al. | |
| 8,721,557 B2* | 5/2014 | Chen | A61B 5/022 600/494 |
| 9,695,101 B2 | 7/2017 | Shaver et al. | |
| 2002/0077535 A1 | 6/2002 | Finarov et al. | |
| 2002/0173709 A1 | 11/2002 | Fine et al. | |
| 2003/0137650 A1 | 7/2003 | Fine et al. | |
| 2004/0176671 A1 | 9/2004 | Fine et al. | |
| 2004/0225205 A1 | 11/2004 | Fine et al. | |
| 2004/0249252 A1 | 12/2004 | Fine et al. | |
| 2005/0101846 A1 | 5/2005 | Fine et al. | |
| 2006/0009685 A1 | 1/2006 | Finarov et al. | |
| 2006/0058690 A1* | 3/2006 | Bartnik | A61B 5/7207 600/504 |
| 2006/0129040 A1 | 6/2006 | Fine et al. | |
| 2006/0195034 A1* | 8/2006 | Skrabal | A61B 5/02255 600/485 |
| 2006/0200014 A1 | 9/2006 | Fine et al. | |
| 2007/0078312 A1 | 4/2007 | Fine et al. | |
| 2007/0232940 A1 | 10/2007 | Fine et al. | |
| 2008/0071180 A1* | 3/2008 | Borgos | A61B 5/7239 600/500 |
| 2008/0183053 A1 | 7/2008 | Borgos et al. | |
| 2008/0183059 A1* | 7/2008 | LaPlante | A61B 5/14539 600/363 |
| 2009/0082642 A1 | 3/2009 | Fine | |
| 2009/0209834 A1 | 8/2009 | Fine | |
| 2010/0106029 A1* | 4/2010 | Fraden | A61B 5/02233 600/493 |
| 2010/0286497 A1 | 11/2010 | Fine et al. | |
| 2010/0324384 A1* | 12/2010 | Moon | A61B 5/14551 600/323 |
| 2011/0033385 A1 | 2/2011 | Fine et al. | |
| 2011/0066044 A1* | 3/2011 | Moon | A61B 5/021 600/485 |
| 2011/0082355 A1 | 4/2011 | Eisen et al. | |
| 2011/0105917 A1 | 5/2011 | Fortin et al. | |
| 2011/0295133 A1 | 12/2011 | Tatara et al. | |
| 2012/0130215 A1 | 5/2012 | Fine et al. | |
| 2013/0131475 A1 | 5/2013 | Eisen et al. | |
| 2013/0253332 A1 | 9/2013 | Hayman et al. | |
| 2014/0094666 A1 | 4/2014 | Fine | |
| 2014/0200423 A1 | 7/2014 | Eisen et al. | |
| 2015/0141766 A1 | 5/2015 | Fine | |
| 2015/0201852 A1 | 7/2015 | Fortin | |
| 2016/0089036 A1* | 3/2016 | Kobayashi | A61B 5/0059 600/480 |
| 2016/0278676 A1 | 9/2016 | Eisen et al. | |
| 2018/0042513 A1* | 2/2018 | Connor | A61B 5/4875 |
| 2018/0153420 A1 | 6/2018 | Fine et al. | |
| 2018/0160913 A1 | 6/2018 | Fine | |

OTHER PUBLICATIONS

Written Opinion for PCT/IL2017/051139 dated Apr. 19, 2018.
International Search Report for PCT/IB2017/053339 dated Oct. 3, 2017.
Written Opinion for PCT/IB2017/053339 dated Oct. 3, 2017.
European application EP35256747.

\* cited by examiner

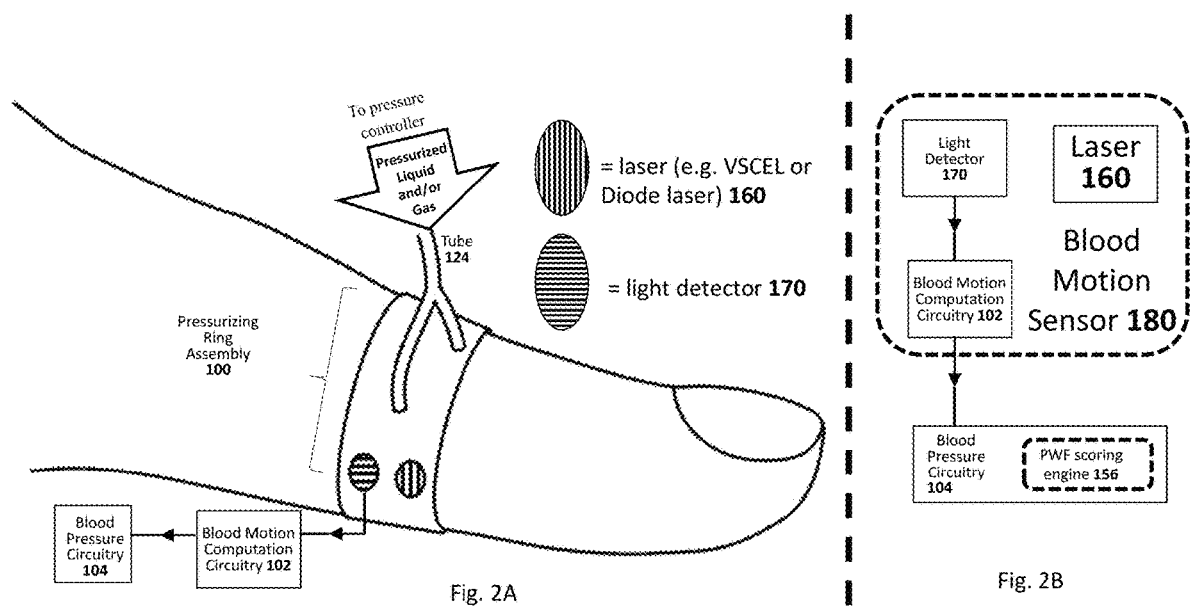

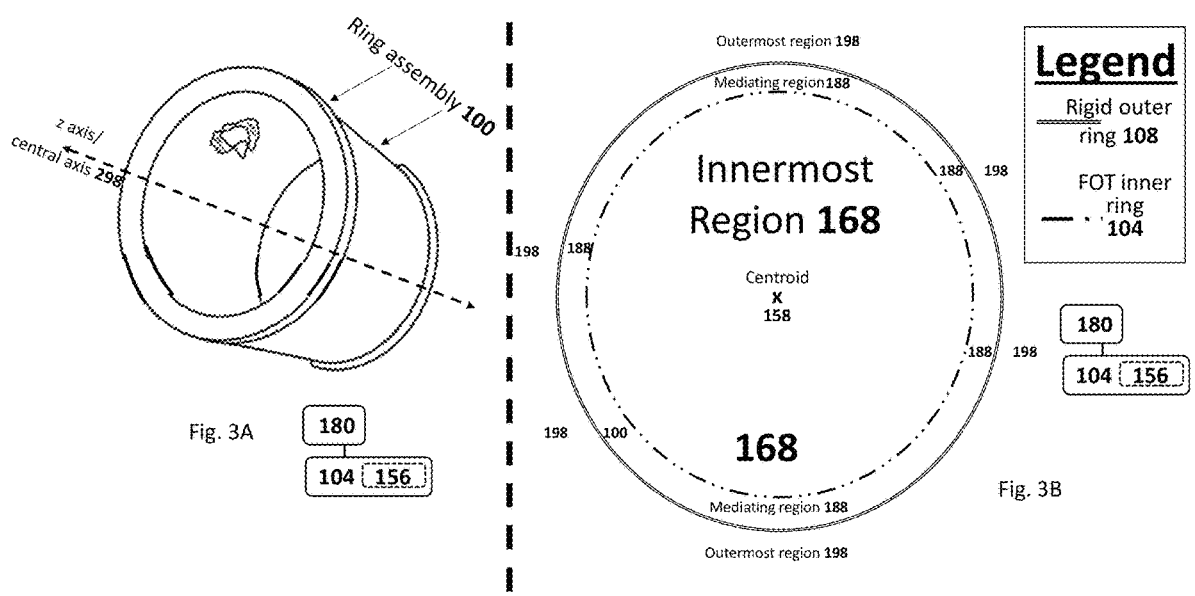

Provide S201 a ring assembly 100 comprising nested outer 108 and inner 104 rings such that:
(i) The inner and outer rings define inner region 168, mediating region 188, and an outermost region 198
(ii) the inner ring 104 comprises a section that is flexible and optically-transparent (FOT),
(iii) the outer ring comprising a rigid section;
(iv) An interior of a gas-sealable chamber is disposed in the mediating region between the FOT section of the inner ring and the rigid section of the outer ring

↓

When biological tissue is disposed in the innermost region, inflating S205 the chamber so as to force the FOT section of the inner ring the apply an inwardly-directed pressure upon the innermost-region-disposed biological tissue

↓

When the cushion is inflated so that FOT section 198 of the inner ring 104 applies pressure to the biological tissue, operating S209 laser and a light detector so that:
 i. light emitted by the laser is scattered by the innermost-region-disposed biological tissue after traversing both the interior of the gas-sealable inflatable chamber and the FOT section of the inner ring;
 ii. the tissue-scattered laser light is received by the light detector after traversing both the FOT section of the inner ring and the interior of the gas-sealable inflatable chamber

↓

Electronically processing S213 output of the light detector to compute therefrom a pressure-applied tissue blood motion signal descriptive of blood motion in the biological tissue when subjected to the inwardly-directed pressure

↓

Computing S217 a systolic and/or diastolic blood pressure of the mammal by correlating a measurement of a gas pressure within the inflatable chamber with the computed pressure-applied tissue blood motion signal

Fig. 10A

Providing 301: (i) a rigid restrictor defining an optically transparent region therein, and
(ii) an inflatable cushion such that at least a portion of a sealing barrier of the inflatable cushion is FOT

↓

Forcing S305 the FOT to apply pressure to the biological tissue by inflating the inflatable cushion so that during inflation of the cushion, a presence of the rigid restrictor restricts a range of motion of gas within the inflated cushion and biases inflation-driven motion of the FOT barrier portion in a direction away from the rigid restrictor

↓

When the cushion is inflated so that the FOT barrier portion applies pressure to the biological tissue, operating S309 laser and a light detector so that:
i. light emitted by the laser is scattered by the pressure-applied biological tissue after passing through the optically transparent region of the rigid restrictor, the pressure-applying FOT barrier portion of the inflated cushion, and the inflated cushion interior
ii. the tissue-scattered laser light is received by the light detector after passing through the pressure-applying FOT barrier portion of the inflated cushion, the inflated cushion interior and the optically transparent region of the rigid restrictor

↓

Electronically processing S313 output of the light detector to compute therefrom a pressure-applied tissue blood motion signal descriptive of blood motion in the biological tissue when subjected to the applied pressure

↓

Computing S317 a systolic and/or diastolic blood pressure of the mammal by correlating a measurement of a gas pressure within the inflatable chamber with the computed pressure-applied tissue blood motion signal

Fig. 10B

Fig. 12A  Non-contact configuration

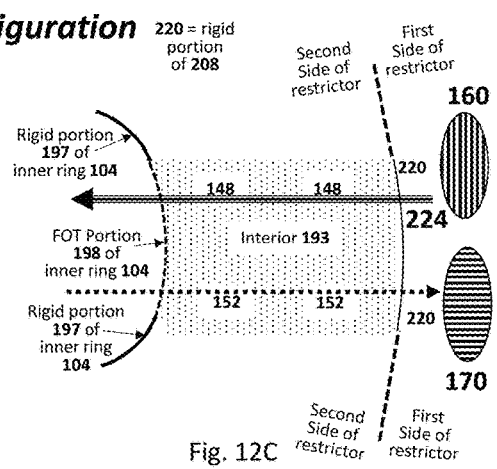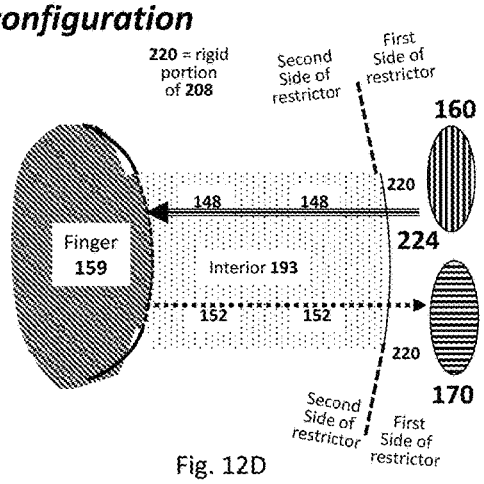
Fig. 12C
Fig. 12D

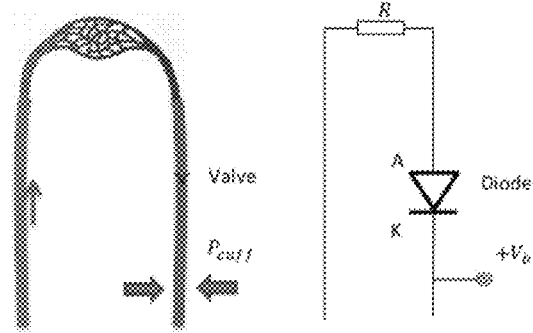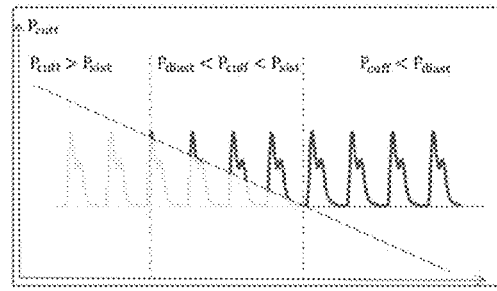
Fig. 18                                                  Fig. 19

METHOD AND APPARATUS FOR OPTICALLY MEASURING BLOOD PRESSURE

CROSS-REFERENCE TO RELATED APPLICATIONS

This patent application is a continuation in part of U.S. patent application Ser. No. 15/474,963 filed on Mar. 30, 2017, which is incorporated by reference in its entirety. U.S. patent application Ser. No. 15/474,963 claims priority to U.S. patent application Ser. No. 62/315,010 filed on Mar. 30, 2016 which is incorporated by reference in its entirety. This patent application also claims priority to U.S. patent application Ser. No. 62/407,429 filed on Oct. 21, 2016, which is incorporated by reference in its entirety.

BACKGROUND

Blood Pressure

Blood pressure is defined as the pressure that is exerted by the blood upon the walls of the blood vessels and especially arteries and that varies with the muscular efficiency of the heart, the blood volume and viscosity, the age and health of the individual, and the state of the vascular wall Blood pressure is recorded as two numbers, such as 120/80. The larger number indicates the pressure in the arteries as the heart pumps out blood during each beat. This is called the systolic blood pressure. The lower number indicates the pressure as the heart relaxes before the next beat. This is called the diastolic blood pressure.

Elevated blood pressure above its 'normal' range is a significant cause of death and disability in the world. Accurate blood pressure measurement is therefore vital in the prevention and treatment of blood-pressure-related diseases. Additionally, in very ill patients, accurate measurement of blood pressure is essential for monitoring cardiovascular homeostasis.

The most accurate non-invasive method of blood pressure measurement is called auscultatory or Korotkoff method. It is based on the observation of the repetitive sounds generated by the blood flow. As the cuff pressure decreases gradually during deflation, the Korotkoff sound changes in intensity and quality, and five different stages can be distinguished. The blood pressure measurement based on Korotkoff sounds using mercury sphygmomanometer currently is regarded as the gold standard method for indirect measurement of blood pressure.

The Wikipedia article about "Sphygmomanometer" states the following:

With a manual instrument, listening with a stethoscope to the brachial artery at the elbow, the examiner slowly releases the pressure in the cuff. As the pressure in the cuffs falls, a "whooshing" or pounding sound is heard (see Korotkoff sounds) when blood flow first starts again in the artery. The pressure at which this sound began is noted and recorded as the systolic blood pressure. The cuff pressure is further released until the sound can no longer be heard. This is recorded as the diastolic blood pressure. In noisy environments where auscultation is impossible (such as the scenes often encountered in emergency medicine), systolic blood pressure alone may be read by releasing the pressure until a radial pulse is palpated (felt). In veterinary medicine, auscultation is rarely of use, and palpation or visualization of pulse distal to the sphygmomanometer is used to detect systolic pressure.

The major disadvantage of this method that this type of measurement needs a physician or specially trained caregiver.

In contrast, home self-monitoring of the blood pressure is preferably performed automatically, obviating the need for requiring a trained care-giver. Typically, commercially available home self-devices employed an oscillometric method of the blood pressure.

Oscillometric measurement devices use an electronic pressure sensor with a numerical readout of blood pressure. In most cases the cuff is inflated and released by an electrically operated pump and valve, which may be fitted on the wrist (elevated to heart height), although the upper arm is preferred. Initially, the cuff is inflated to a pressure in excess of the systolic arterial pressure, and then the pressure reduces to below diastolic pressure. Once the blood flow is present, but restricted, the cuff pressure will vary periodically in synchrony with the cyclic expansion and contraction of the brachial artery. The values of systolic and diastolic pressure are computed from the raw data, using a specially adjusted algorithm. Most of the oscillometric algorithms rely on empirical coefficients for systolic and diastolic pressure evaluation that may differ in various patient populations. This makes this technique less accurate and reliable than auscultatory method.

Optical Blood Motion Sensors

For the present disclosure, a 'blood motion' sensor measures motion of blood or any component (e.g. blood plasma, red blood cells (RBCs) suspended in blood plasma) thereof through blood vessels (e.g. skin capillaries).

Types of blood motions sensors include blood flow sensors (e.g. laser-Doppler sensors, or DLS (dynamic-light-scattering) sensors), pulse sensors (PPG) techniques or laser-Doppler-based pulse wave sensors or DLS-based pulse wave sensors).

One salient feature of blood motion sensors, especially PPG based sensors, is that it is desirable for direct contact between a light source of the sensor and the subject's skin—this allows for the most accurate measurement of blood motion, and in the case of PPG is an enabling required—i.e. without such direct contact, meaningful measurement of blood flow may be impossible.

DLS Sensors

PPG and laser-Doppler sensors have been known in the art for many decades. In contrast, DLS sensors (used interchangeably with 'DLS devices') were disclosed much more recently. Thus, in recent years, it has been disclosed to employ dynamic light scattering techniques (DLS) to measure pulse, blood pressure, blood plasma viscosity, and other hemodynamic parameters—see WO 2008/053474, WO/2011/013132, WO/2012/064326, and WO/2016/185244, each of which are incorporated by reference.

WO 2008/053474 and WO/2012/064326, both incorporated by reference, disclose detecting and analyzing a fluctuation-dependent speckle pattern by dynamic light scattering techniques. It is disclosed that the blood pressure may be computed according to the results of the analysis. The DLS method is based on the effect of coherent light scattering on moving particles. In the case of the measurement of blood pressure the Red Blood Cells (RBC's) moving in the arterial and capillary blood path are responsible for the measured DLS-related signal. In addition, WO/2012/064326 discloses an apparatus comprising first and second photodetectors configured to respectively generate first and second analog signals from light incident thereon. Analog circuitry generates a difference analog signal from the first and second analog signal and this difference analog signal is analyzed, for example, using DLS techniques and/or to detect blood pressure.

When optically probing pulsatile blood, DLS devices work as follows: (i) a portion of the subject's skin or tissue is illuminated by source of coherent light (e.g. a VCSEL (vertical cavity surface emitting laser) or a diode laser) to scatter partially or entirely coherent light off of the subject's moving red blood cells (RBCs) to induce a scattered-light time-dependent and shear-rate dependent optical response; (ii) the scattered light from the illuminated skin or tissue is received by a photodetector(s) to generate an electrical signal descriptive of the induced scattered-light time-dependent optical response; (iii) the scattered-light-optical-response-descriptive electrical signal or a derived-signal thereof is processed (e.g. by any combination of analog circuitry, digital circuitry such as a digital computer, firmware and/or software) to compute therefrom one or more blood-shear-rate-descriptive (BSRD) signal(s). This processing of the scattered-light-optical-response-descriptive electrical signal or a derived-signal thereof may be performed by computing an autocorrelation of the scattered-light-optical-response-descriptive electrical signal or by computing a power spectrum thereof.

FIG. 11B of WO 2008/053474 illustrates an example of a BSRD signal(s) that describes a pulsatile pressure wave—i.e. a pulsatile BSRD. As discussed in WO 2008/053474, the pulsatile BSRD may be analyzed, for example, to compute a subject's pulse rate.

In contrast to PPG devices, which may only be used to measure systolic blood pressure, WO 2008/053474 teaches that DLS devices may be used to measure systolic or diastolic blood pressure.

Optical Blood Pressure Sensors

US 20120179011 discloses a body-worn system that continuously measures pulse oximetry and blood pressure, along with motion, posture, and activity level, from an ambulatory patient. FIG. 1 (PRIOR ART) roughly corresponds to one of the figures of US 20120179011 and shows that the system of US 20120179011 includes: (i) an inflatable cuff disposed on the subject's upper arm and (ii) a PPG device disposed 'downstream' to the inflatable cuff on the subject's finger.

Thus, in US 20120179011 there is a longitudinal displacement (e.g. on the order of magnitude of 30-70 centimeters) between (i) the 'blood occluding location' where a pressure-applying surface (i.e. of the cuff) applies a blood-occluding pressure on the subject to occlude blood flow at downstream locations and (ii) the blood-motion measurement location where blood motion (i.e. in the example of US 20120179011 this is pulse) is optically measured. As shown in FIG. 1, this measurement location is significantly distal (i.e. towards the subject's fingertip) to the pressure-applying surface.

US 20120179011 is not the only disclosure of optical blood pressure sensors—other disclosures of optical blood pressure sensors appear in the literature (e.g. see WO 2008/053474).

There is an ongoing need for accurate and easy-to-use blood pressure sensors, suitable for home use. To date, market adaption of optical pressure sensing technology has been minimal at best.

SUMMARY OF EMBODIMENTS

Embodiments of the invention relate to a system for optically measuring systolic and/or diastolic blood pressure of a mammalian subject (e.g. human—for example, a baby or adult), the system comprising an (i) optical blood motion sensor for detecting blood motion by laser light and (ii) a gas-sealable and inflatable pressurizing cushion (e.g. a cuff) which when inflated, applies over-systolic pressure to the subject's skin.

In different embodiments, (i) the pressurizing cushion comprises a sealing barrier portion that is both flexible and optically transparent (FOT); and (ii) the pressurizing cushion is mechanically coupled to a rigid restrictor having an optically transparent region (e.g. optically-transparent material or a window/void) therein. A presence of the rigid restrictor is useful for reducing the amount of time required to inflate the pressurizing cushion to at least systolic pressure and/or for distributing applied pressure so that it is relatively uniform around the circumference of a finger or toe.

When the cushion is sealed and inflated with pressured gas or liquid, pressurized gas or liquid within the cushion applies pressure to the biological tissue via the FOT sealing portion barrier—thus, the FOT sealing portion barrier is 'pressure-applying.' At this time, the optical blood motion sensor (i.e. comprising a laser, a light detector and electronic circuitry) measures blood motion within the biological tissue to which the pressure is applied by the FOT sealing portion.

According to the known principles of operation of PPG sensors, direct contact between the laser and the biological tissue would be required. That is not the case here. Instead, according to embodiments of the invention, both the FOT portion of the sealing barrier and an interior of the cushion are disposed between the laser and the biological tissue. Thus, the laser illuminates the biological tissue via the cushion interior and the FOT portion of the sealing barrier, both of which are disposed along an optical path between the laser and the biological tissue—in this manner the blood motion sensor is disposed in a 'non-contact configuration' and measure blood flow while in the non-contact configuration.

In some preferred embodiments, the rigid restrictor has an optically transparent region, through which laser light passes through en route to the biological tissue. This is one particular example of operating in 'non-contract configuration.' In these embodiments, the rigid restrictor has an optically transparent region and the laser illuminates the biological tissue via: (i) the optically transparent region of the rigid restrictor; (ii) the cushion interior and (iii) the FOT portion of the sealing barrier.

In this manner, it is possible to achieve two potentially conflicting goals: (i) to optically measure blood motion specifically at a tissue location where pressure is applied to the tissue (i.e. rather than measuring at a downstream location where the prevailing blood-flow may be different) for the purpose of deriving from the optical blood-motion measurement systolic and/or diastolic blood pressure; and (ii) to do this in a manner where the optical blood motion sensor does not mechanically interfere with the application of pressure upon the biological tissue.

This mechanical interference, which may now be avoided, would exist if the blood motion sensor were to direct contact the biological tissue (i.e. as would be required for pulse oximetry devices). This mechanical interference, which may now be avoided, could: (i) make it difficult if not impossible to apply a uniform pressure around the circumference of a finger or toe and/or (ii) make it difficult to accurately measure the applied pressure applied upon the biological tissue. In difference embodiments, because this mechanical interference is avoided, the internal pressure within the inflated cushion (which is easily measured) accurately reflects the applied pressure on the biological tissue—it is believed that this would not be the case if biological pressure were applied via the optical blood motion sensor (something which may now be avoided thanks to the presently-disclosed optical features of the cushion and/or restrictor).

Although it is axiomatic in the art of PPG that direct contact between a light source and the subject's skin is required, embodiments of the present invention adapt a different approach, as noted above. Instead of requiring direct contact between (i) the optical blood motion sensor and (ii) the subject's skin, the presently apparatus is configured so that laser light must first pass through the FOT portion of the sealing barrier of the inflated cushion, optionally through an interior of the cushion and optionally through the optically transparent region of the rigid restrictor en route to illuminate the biological tissue. Embodiments of the invention further provide the feature that scattered (e.g. reflected) laser light from the illuminated biological tissue returns to a light detector of the optical blood motion sensor after passing through the FOT portion of the sealing barrier of the inflated cushion, and optionally through the interior of the cushion and optionally through the optically transparent region of the rigid restrictor.

A method of optically measuring blood pressure of a mammal, the method comprising: a. providing a ring assembly comprising nested outer and inner rings disposed around a central axis, the inner ring comprising a section that is flexible and optically-transparent (FOT), the outer ring comprising a rigid section, the outer and inner rings defining the following three regions: i. an innermost region within the inside of the inner ring; ii. an annular-shaped mediating region outside of the inner ring and within the outer ring; iii. an outermost region exterior to the outer ring, an interior of a gas-sealable inflatable chamber being disposed in the mediating region between the FOT section of the inner ring and the rigid section of the outer ring; b. when biological tissue of the mammal is disposed in the innermost region, inflating the chamber, so as to force the FOT section of the inner ring to apply an inwardly-directed pressure upon the innermost-region-disposed biological tissue; c. when the cushion is inflated so that the FOT section of the inner ring applies inward pressure to the biological tissue, operating a laser and a light detector so that: i. light emitted by the laser is scattered by the innermost-region-disposed biological tissue after traversing both the interior of the gas-sealable inflatable chamber and the FOT section of the inner ring; ii. the tissue-scattered laser light is received by the light detector after traversing both the FOT section of the inner ring and the interior of the gas-sealable inflatable chamber; d. electronically processing output of the light detector to compute therefrom a pressure-applied tissue blood motion signal descriptive of blood motion in the biological tissue when subjected to the inwardly-directed pressure; and e. computing a systolic and/or diastolic blood pressure of the mammal by correlating a measurement of a pressure within the inflatable chamber (i.e. a pressure of gas or liquid disposed within the inflatable chamber) with the computed pressure-applied tissue blood motion optical signal.

In some embodiments, the rigid section of the outer ring comprises an optically transparent region therein through which the laser light emitted by the laser passes through before passing traversing both the interior of the gas-sealable inflatable chamber and the FOT section of the inner ring en route to the biological tissue.

In some embodiments, after traversing both the FOT section of the inner ring and the interior of the gas-sealable inflatable chamber, the tissue-scattered laser light passes through the optically transparent region of the rigid section of the outer ring en route to the light detector.

In some embodiments, the optically transparent region of the rigid section of the outer ring is void(s) within the outer ring.

In some embodiments, the optically transparent region of the rigid section of the outer ring is optically-transparent material of the rigid section of the outer ring.

In some embodiments, outer ring comprises one or more of the rigid section(s) which collectively span at least 180 degrees or at least 270 degrees or at least 315 degrees or at least 330 degrees around the central axis.

In some embodiments, the gas-sealable chamber, by itself or together with additional inflated gas-sealable chambers disposed in the mediating section, inwardly applies pressure upon the biological tissue in the mediating region via locations of the inner ring which collectively span at least 180 degrees or at least 270 degrees or at least 315 degrees or at least 330 degrees around the central axis.

In some embodiments, an inner surface of the outer ring is not in fluid communication with an interior of the gas-sealable chamber whose inflation drives pressure upon the biological tissue by the FOT section of the inner ring.

In some embodiments, the FOT section of the inner ring is part of a larger barrier around an interior of the gas-sealable chamber, an entirety of which is not optically transparent and/or an entirety of which is not flexible.

A system for optically measuring blood pressure of a mammal, the system comprising: a. a ring assembly comprising nested outer and inner rings disposed around a central axis, the inner ring comprising a section that is flexible and optically-transparent (FOT), the outer ring comprising a rigid section, the outer and inner rings defining the following three regions: i. an innermost region within the inside of the inner ring; ii. an annular-shaped mediating region outside of the inner ring and within the outer ring; iii. an outermost region exterior to the outer ring, an interior of a gas-sealable inflatable chamber being disposed in the mediating region between the FOT section of the inner ring and the rigid section of the outer ring so that when biological tissue is disposed in the innermost region, inflation of the chamber forces the FOT section of the inner ring to apply an inwardly-directed pressure upon the innermost-region-disposed biological tissue; b. an optical blood-motion sensor comprising a laser and a light detector, both of which are disposed exterior to the inner ring and both of which inwardly face towards the innermost region so that when the biological tissue is innermost-region-disposed and the FOT section of the inner region applies thereon the inwardly-directed pressure: i. light emitted by the laser is scattered by the innermost-region-disposed biological tissue after traversing both the interior of the gas-sealable inflatable chamber and the FOT section of the inner ring; ii. the tissue-scattered laser light is received by the light detector after traversing both the FOT section of the inner ring and the interior of the gas-sealable inflatable chamber; and iii. output of the light detector is electronically processed to compute therefrom a pressure-applied tissue blood motion signal descriptive of blood motion in the biological tissue when subjected to the inwardly-directed pressure; and c. blood pressure circuitry configured to compute a systolic and/or diastolic blood pressure of the mammal by correlating a measurement of a pressure (i.e. a pressure of gas or liquid disposed within the inflatable chamber) within the inflatable chamber with the pressure-applied tissue blood motion signal computed by the optical blood-movement sensor.

In some embodiments, the rigid section of the outer ring comprises an optically transparent region, and wherein the laser is disposed and oriented so that the laser light emitted by the laser passes through before passing traversing both the interior of the gas-sealable inflatable chamber and the FOT section of the inner ring en route to the biological tissue.

In some embodiments, the light detector is disposed so that after traversing both the FOT section of the inner ring and the interior of the gas-sealable inflatable chamber, the tissue-scattered laser light passes through the optically transparent region of the rigid section of the outer ring en route to the light detector.

In some embodiments, the optically transparent region of the rigid section of the outer ring is void(s) within the outer ring.

In some embodiments, the optically transparent region of the rigid section of the outer ring is optically-transparent material of the rigid section of the outer ring.

In some embodiments, the outer ring comprises one or more of the rigid section(s) which collectively span at least 180 degrees or at least 270 degrees or at least 315 degrees or at least 330 degrees around the central axis.

In some embodiments, the gas-sealable chamber, by itself or together with additional inflated gas-sealable chambers disposed in the mediating section, inwardly applies pressure upon the biological tissue in the mediating region via locations of the inner ring which collectively span at least 180 degrees or at least 270 degrees or at least 315 degrees or 330 degrees around the central axis.

In some embodiments, an inner surface of the outer ring is not in fluid communication with an interior of the gas-sealable chamber whose inflation drives pressure upon the biological tissue by the FOT section of the inner ring.

In some embodiments, the FOT section of the inner ring is part of a larger barrier around an interior of the gas-sealable chamber, an entirety of which is not optically transparent and/or an entirety of which is not flexible.

A method for optically measuring a systolic and/or diastolic blood pressure of a mammal, the method comprising: a. providing a rigid restrictor defining an optically transparent region therein, and an inflatable cushion, at least a portion of a sealing barrier of the inflatable cushion being flexible and optically transparent (FOT); b. forcing the FOT to apply pressure to biological tissue of the mammal by inflating the inflatable cushion so that during inflation of the cushion, a presence of the rigid restrictor restricts a range of motion of gas or liquid within the inflated cushion and biases inflation-driven motion of the FOT barrier portion in a direction away from the rigid restrictor; c. when the cushion is inflated so that the FOT barrier portion applies pressure to the biological tissue, operating a laser and a light detector so that: A. light emitted by the laser is scattered by the pressure-applied biological tissue after passing through the optically transparent region of the rigid restrictor, the pressure-applying FOT barrier portion of the inflated cushion, and the inflated cushion interior; and B. the tissue-scattered laser light is received by the light detector after passing through the pressure-applying FOT barrier portion of the inflated cushion, the inflated cushion interior and the optically transparent region of the rigid restrictor; d. electronically processing output of the light detector to compute therefrom a pressure-applied tissue blood motion signal descriptive of blood motion in the biological tissue when subjected to the applied pressure; and e. computing a systolic and/or diastolic blood pressure of the mammal by correlating a measurement of a pressure (i.e. a pressure of gas or liquid disposed within the inflatable cushion) within the inflated cushion with the computed pressure-applied tissue blood motion signal.

In some embodiments, the rigid restrictor has first and second sides that face away from each other; the laser and the light detector are disposed on a first side of the rigid restrictor; and the cushion interior is disposed on the second side thereof.

In some embodiments, the laser is oriented so that laser light emitted from the laser passes through a thickness of the rigid restrictor.

In some embodiments, at least a portion of the cushion is formed by the rigid restrictor.

In some embodiments, the cushion interior is gas-sealed from the rigid restrictor.

In some embodiments, the FOT barrier portion is part of a larger barrier, an entirety of which is not optically transparent and/or an entirety of which is not flexible.

In some embodiments, the optically transparent region of the rigid restrictor is defined by void(s) therein.

In some embodiments, at least a portion of the rigid restrictor is constructed from optically-transparent material which is present in the optically transparent region.

A system for optically measuring a systolic and/or diastolic blood pressure of a mammal, the system comprising: a. a rigid restrictor defining an optically transparent region therein; b. an inflatable cushion, at least a portion of a sealing barrier of the inflatable cushion being flexible and optically transparent (FOT), the cushion being mechanically coupled to the rigid restrictor so that during inflation of the cushion, a presence of the rigid restrictor restricts a range of motion of gas or liquid within the inflated cushion and biases inflation-driven motion of the FOT barrier portion in a direction away from the rigid restrictor; c. an optical blood-motion sensor comprising a laser and a light detector both of which are attached to the rigid restrictor and oriented so that when the cushion is inflated so that the FOT barrier portion applies pressure to biological tissue of the mammal: A. light emitted by the laser is scattered by the pressure-applied biological tissue after passing through the optically transparent region of the rigid restrictor, the pressure-applying FOT barrier portion of the inflated cushion, and the inflated cushion interior; and B. the tissue-scattered laser light is received by the light detector after passing through the pressure-applying FOT barrier portion of the inflated cushion, the inflated cushion interior and the optically transparent region of the rigid restrictor; iii. output of the light detector is electronically processed to compute therefrom a pressure-applied tissue blood motion signal descriptive of blood motion in the biological tissue when subjected to the applied pressure; and c. blood pressure circuitry configured to compute a systolic and/or diastolic blood pressure of the mammal by correlating a measurement of a pressure (i.e. a pressure of gas or liquid disposed within the inflatable cushion) within the inflated cushion with the pressure-applied tissue blood motion signal computed by the optical blood-movement sensor.

In some embodiments, the rigid restrictor has first and second sides that face away from each other; the laser and the light detector are disposed on a first side of the rigid restrictor; and the cushion interior is disposed on the second side thereof.

In some embodiments, the laser is oriented so that laser light emitted from the laser passes through a thickness of the rigid restrictor.

In some embodiments, at least a portion of the cushion is formed by the rigid restrictor.

In some embodiments, the cushion interior is gas-sealed from the rigid restrictor.

In some embodiments, the FOT barrier portion is part of a larger barrier, an entirety of which is not optically transparent and/or an entirety of which is not flexible.

In some embodiments, the optically transparent region of the rigid restrictor is defined by void(s) therein.

In some embodiments, at least a portion of the rigid restrictor is constructed from optically-transparent material which is present in the optically transparent region.

In some embodiments, the rigid restrictor has an annular cross section or is a portion of annular-shaped assembly.

In some embodiments, the rigid restrictor has an annular cross section or is a portion of annular-shaped assembly.

A method for optically measuring a systolic and/or diastolic blood pressure of a mammal, the method comprising: a. providing an inflatable cushion, at least a portion of a sealing barrier of the inflatable cushion being flexible and optically transparent (FOT); b. forcing the FOT to apply pressure to biological tissue of the mammal by inflating the inflatable cushion so as to force the FOT barrier portion to apply pressure to the biological tissue; c. when the cushion is inflated so that the FOT barrier portion applies pressure to the biological tissue, operating a laser and a light detector so that: A. light emitted by the laser is scattered by the pressure-applied biological tissue after passing through the pressure-applying FOT barrier portion of the inflated cushion, and the inflated cushion interior; and B. the tissue-scattered laser light is received by the light detector after passing through the pressure-applying FOT barrier portion of the inflated cushion, and the inflated cushion interior; d. electronically processing output of the light detector to compute therefrom a pressure-applied tissue blood motion signal descriptive of blood motion in the biological tissue when subjected to the applied pressure; and e. computing a systolic and/or diastolic blood pressure of the mammal by correlating a measurement of a pressure (i.e. a pressure of gas or liquid disposed within the inflatable chamber) within the inflated cushion with the computed pressure-applied tissue blood motion signal.

In some embodiments, the blood-movement sensor is a laser Doppler sensor.

In some embodiments, the blood-movement sensor is a dynamic-light-scattering (DLS) sensor for computing from light received by the light-detector a blood-shear-rate-descriptive (BSRD) signal(s) from output of the light detector thereof.

In some embodiments, the blood-movement sensor is at least one of: i. a blood-flow sensor for computing a blood flow within the tissue; ii. a pulse wave sensor for computing one or more feature(s) of a pulse wave signal of the organism from the reflected light received by the light detector.

In some embodiments, the laser and the light-sensor are part of a laser Doppler sensor that includes electronic circuitry which electronically processes the output of the light detector.

In some embodiments, the laser and the light-sensor are part of the blood-movement sensor comprising electronic circuitry which processes output of the light detector to compute therefrom a blood-shear-rate-descriptive (BSRD) signal(s).

In some embodiments, the laser and the light-sensor are part of a blood-movement sensor selected from the group consisting of: i. a blood-flow sensor for computing a blood flow within the tissue; ii. a pulse wave sensor for computing one or more feature(s) of a pressure wave signal of the organism from the reflected light received by the light detector.

In some embodiments, the electronic processing of step (d) and the resulting pressure-applied tissue blood motion signal is based on light from tissue-scattered laser light that is received by the light detector when the cushion is only partially inflated.

In some embodiments, wherein the inflating of the chamber or cushion is performed to define a ramp-up phase, and is followed by a deflating of the chamber or cushion to define a ramp-down phase.

In some embodiments, the electronic processing of step (d) and the resulting pressure-applied tissue blood motion signal is based on light from tissue-scattered laser light that is received by the light detector during the ramp-up phase.

In some embodiments, the electronic processing of step (d) and the resulting pressure-applied tissue blood motion signal is based on light from tissue-scattered laser light that is received by the light detector during the ramp-down phase.

In some embodiments, the correlated pressure measurement (i.e. a pressure of gas or liquid disposed within the inflatable chamber or cushion) is a measurement of the gas or liquid pressure within the inflatable chamber or cushion during the ramp-up of ramp-down phase.

In some embodiments, the systolic blood pressure of the mammal is computed by detecting a magnitude of pressure (i.e. a pressure of gas or liquid disposed within the inflatable chamber or cushion) when a pulsatile wave form appears or disappears within the pressure-applied tissue blood motion signal.

In some embodiments, the disastolic blood pressure of the mammal is computed by scoring respective prominences of waveform-shape feature(s) of consecutive pulsatile waveforms within the pressure-applied tissue blood motion signal and comparing the scores to each other.

In some embodiments, one or more of the waveform-shape feature(s) is a feature of a post-peak and pre-trough portion of the pulsatile wave.

In some embodiments, the waveform-shape feature is a prominence of a dicrotic notch.

A method for measuring systolic and diastolic blood pressure of a mammal, the method comprising: a. bringing biological tissue of the mammal into contact with a pressure-applying surface; b. ramping up a magnitude of force applied by the force-applying surface upon biological tissue to at least over-systolic pressure; c. subsequently, ramping down the magnitude of the applied pressure within a range below systolic pressure; d. during the pressure ramp-up or pressure ramp-down, performing the following: i. acquiring pressure measurement data by measuring the magnitude of the pressure applied by the pressure-applying surface upon the biological tissue; ii. operating a DLS sensor to laser-illuminate a tissue-surface of the biological tissue so that laser-light reflected by and/or transmitted by and/or scattered by the biological tissue is received into a light-detector of the DLS sensor and electronically processed to compute a RBC-relative-motion-descriptive signal (RRMDS) describing relative motion of RBCs suspended in the blood plasma; e. analyzing a relation between the pressure-measurement data and the RRMDS of the biological tissue during the ramp-up or during the ramp-down so as to: i. computing the systolic blood pressure of the organism by detecting a magnitude of a pressure applied by the pressure-applying surface when a pulsatile waveform appears or disappears in the RRMDS; ii. analyze the RRMDS for the time-period when the applied pressure magnitude is below the systolic blood pressure so as to analyze waveform-shape feature(s) of the RRMDS for each pulse cycle of a plurality of pulse cycles; iii. for each pulse cycle of the plurality of pulse cycles, scoring a prominence within the RRMDS of one or more pulsatile waveform-shape features; iv. computing a magnitude of the diastolic pressure by comparing a prominence of pulsatile-waveform features between different pulse cycles.

A method for measuring systolic and diastolic blood pressure of a mammal, the method comprising: a. bringing biological tissue of the mammal into contact with a pressure-applying surface; b. ramping up a magnitude of force applied by the force-applying surface upon biological tissue to at least over-systolic pressure; c. subsequently, ramping down the magnitude of the applied pressure within a range below systolic pressure; d. during the pressure ramp-up or pressure ramp-down, performing the following: i. acquiring pressure measurement data by measuring the magnitude of the pressure applied by the pressure-applying surface upon the biological tissue; ii. operating a blood-motion sensor to laser-illuminate a tissue-surface of the biological tissue so that laser-light reflected by and/or transmitted by and/or scattered by the biological tissue is received into a light-detector of the blood-motion sensor and electronically processed to compute a blood-motion signal (BMS) describing blood motion; e. analyzing a relation between the pressure-measurement data and the BMS of the biological tissue during the ramp-up or during the ramp-down so as to: i. computing the systolic blood pressure of the organism by detecting a magnitude of a pressure applied by the pressure-applying surface when a pulsatile waveform appears or disappears in the BMS; ii. analyze the BMS for the time-period when the applied pressure magnitude is below the systolic blood pressure so as to analyze waveform-shape feature(s) of the BMS for each pulse cycle of a plurality of pulse cycles; iii. for each pulse cycle of the plurality of pulse cycles, scoring a prominence within the BMS of one or more pulsatile waveform-shape features; iv. computing a magnitude of the diastolic pressure by comparing a prominence of pulsatile-waveform features between different pulse cycles.

In some embodiments, one or more of the waveform-shape feature(s) is a feature of a post-peak and pre-trough portion of the pulsatile wave.

In some embodiments, the waveform-shape feature is a prominence of a dicrotic notch.

In some embodiments, at least a diastolic blood pressure is measured.

BRIEF DESCRIPTION OF THE DRAWINGS

Some embodiments of the printing system are described herein with reference to the accompanying drawings. The description, together with the figures, makes apparent to a person having ordinary skill in the art how the teachings of the disclosure may be practiced, by way of non-limiting examples. The figures are for the purpose of illustrative discussion and no attempt is made to show structural details of an embodiment in more detail than is necessary for a fundamental understanding of the disclosure. For the sake of clarity and simplicity, some objects depicted in the figures are not to scale.

FIGS. 2A-2C, 3A-3B, 4A-4D, 5A-5B, 6, 7A-7C, 8A-8B, 9A-9D, 11A-11B, 12A-12D, 15A-15C, and 17A-17D illustrate optical blood-pressure sensors or components thereof;

FIGS. 10A-10B and 16 are flow charts of methods for optically measuring blood pressure.

FIGS. 18-20 present examples related to a theoretical discussion about measuring systolic and/or diastolic blood pressure, based on the measurement of peripheral blood flow.

DESCRIPTION OF EMBODIMENTS OF THE INVENTION

Figure 1:
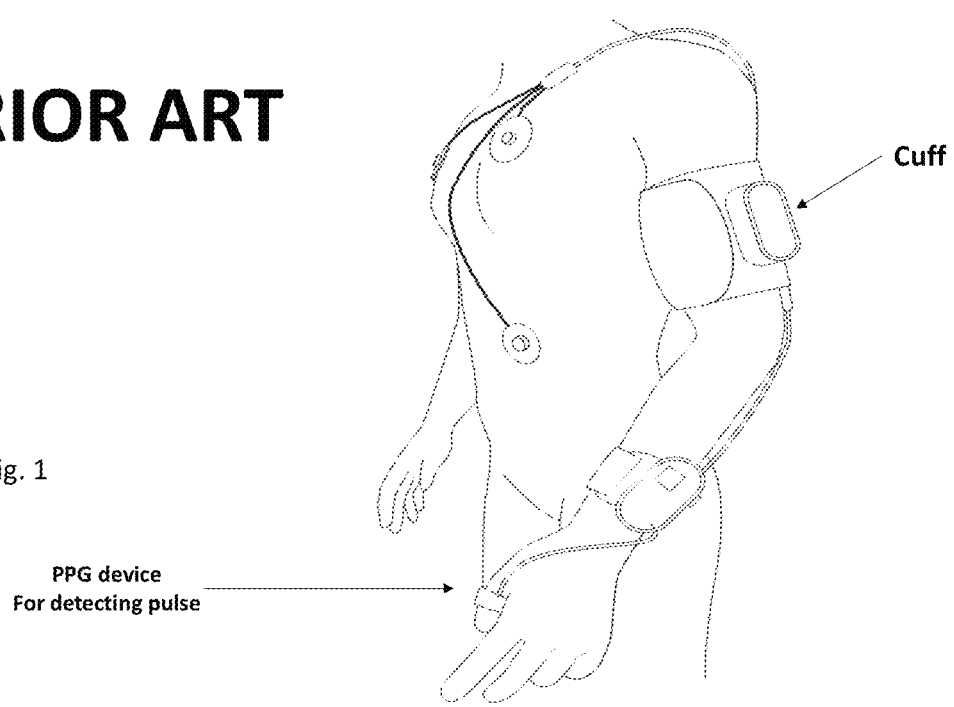
FIG. 1 (PRIOR ART) illustrates: (i) an inflatable cuff disposed on the subject's upper arm and (ii) a PPG device disposed 'downstream' to the inflatable cuff on the subject's finger.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice. Throughout the drawings, like-referenced characters are generally used to designate like elements.

Definitions

For the present disclosure, the term 'optically transparent' refers to light transparent for at least a portion (i.e. at least one wavelength) of the visible and/or infrared (IR) spectra (e.g. near-IR (NIR) spectra up to 1200 nm or at up to 1100 nm or up to 1000 nm).

For the present disclosure, the term 'optically transparent' means transparent to at least a one wavelength of light in the visible and/or infrared (IR) spectrum. In some embodiments, 'optically transparent' refers to transparent to at least one wavelength in the near-infrared (NIR) spectrum.

A 'flexible' object (e.g. barrier portion or inner ring portion) has sufficient flexibility for its intended purpose—i.e. to deform in response to inflation of an inflatable cushion or chamber that is mechanically coupled to the 'flexible' object so as to transfer force from the interior of the inflatable cushion or chamber to a third object (i.e. biological tissue). In some embodiments, any flexible object may be defined by a Shore hardness (e.g. of the inner 104 ring surface) of at most 30 or at most 25 or at most 20, and further optionally, the Shore hardness is at least 10 or at least 15.

For the present disclosure, a 'portion' of an object refers to 'at least a portion.' A 'section' of an object refers to 'at least a section.' Portion and section may be used interchangeably.

For the present disclosure, when an object (e.g. a rigid restrictor or a rigid section of an outer ring) has an 'optically transparent region' the 'optically transparent region' may be any combination of (i) 'optically transparent' material of the object and/or (ii) empty space (e.g. a void or recess or window) within (and defined by) the object—e.g. a canal or window through which visible and/or IR/or NIR light passes.

For the present disclosure, when a cushion or chamber is 'inflated' it is 'at least partially inflated.' In any embodiment, this may be 'at least partially inflated to at least over-systolic pressure.'

For the present disclosure, 'electrical circuitry' or 'electronic circuitry' (or any other 'circuitry' such as 'blood pressure circuitry' or 'control circuitry' or 'pump control circuitry') may include any combination of analog and/or digital circuitry and/or software/computer readable code module and/or firmware and/or hardware element(s) including but not limited to a CPU, volatile or non-volatile memory, field programmable logic array (FPLA) element(s), hard-wired logic element(s), field programmable gate array (FPGA) element(s), and application-specific integrated circuit (ASIC) element(s). Any instruction set architecture may be used including but not limited to reduced instruction set computer (RISC) architecture and/or complex instruction set computer (CISC) architecture.

Non-Contact configuration—Some embodiments of the present invention relate to a system and method of optically measuring systolic and/or diastolic blood pressure based upon optically measuring a blood motion signal (e.g. a pulsatile signal) at a location where pressure is applied to biological tissue, rather than at a 'downstream' location as illustrated in FIG. 1. The blood motion is electronically correlated with a magnitude of pressure applied on the biological tissue.

Instead of requiring contact between a laser of an optical blood motion sensor and the biological tissue (as would be necessary in pulse oximeters), it is possible to operate the optical blood motion sensor in a 'non-contact configuration.' In this non-contact configuration, en route to biological tissue, laser light must first traverse at least one of (e.g. any combination of) a flexible and optically transparent (FOT) barrier section of a pressure-applying cushion and/or an interior of the cushion and/or an optically-transparent region of a rigid restrictor (e.g. the laser light must traverse all three). In this manner the blood motion sensor is disposed in a 'non-contact configuration' and measure blood flow while in the non-contact configuration.

Examples of blood flow sensor operating while in the 'non-contact configuration' are shown in FIGS. 4A-4D, 5A-5B, 6, 7A-7C, 8A-8B, 9A-9D, 11A-11B, 12A, 12C-12D, 15A all of which are discussed in greater detail below. In contrast, in the example of FIG. 15B blood motion sensor 180 is in direct contact with biological tissue (i.e. finger 159) (in a 'contact' configuration)—thus, the chance of mechanical interference from blood motion sensor 180 is greater in the example of FIG. 15B.

Rigid Restrictor—A presence of the rigid restrictor serves to reduce the amount of time required to inflate the cushion and/or serves to evenly distribute applied pressure around a circumference of the subject's finger of toe. One example of a 'rigid restrictor' is rigid outer ring 108 of an annular-shaped ring assembly (see, for example, FIG. 4B, discussed below). When the restrictor is circular shapes like outer ring 108, this prevents pressurized gas (or liquid) within chamber 120 from occupied space outside of outer ring 108, thus 'restricting' a range of motion of the pressurized gas (or liquid).

As will be discussed below, in the examples of FIGS. 4A-4D, 5A-5B, 6, 7A-7C, 8A-8B, 9A-9B, 11A-11B, 12A, 12C-12D, 15A blood flow sensor 180 is both (i) in a non-contact configuration and (ii) in a configuration where the blood floor sensor 180 and the biological tissue 159 where blood pressure is measured are disposed on opposite sides of the rigid restrictor (e.g. at least a portion of outer shell 108). In contrast, in the example of FIGS. 9C-9D, blood floor sensor 180 is also disposed in a 'non-contact configuration'—however, in the example of FIGS. 9C-9D blood floor sensor 180 and the biological tissue 159 are disposed on the same side of rigid restrictor 108. Without limiting the scope of the invention, it is believed that the configuration of FIGS. 9C-9D may be preferable to situations of 'contact configuration' (i.e. less mechanical interference) but less preferable to situations like those of FIGS. 9A-9B where in addition to non-contact configuration, the sensor 180 and the tissue 159 are on 'opposite rides' of the rigid restrictor for even less mechanical interference.

A Discussion of FIGS. 2A-2C, 3A-3B, 4A-4D, 5A-5B, 6, 7A-7C, 9A-9D, 12A, 12C-12D, 15A-15C FIGS. 2A-2C, 3A-3B, 4A-4D, 5A-5B, 6, 7A-7C, 9A-9D, 12A, 12C-12D, 15A-15C relate to apparatus for measuring systolic and/or diastolic blood pressure comprising a ring assembly. In contrast, the apparatus for measuring systolic and/or diastolic blood pressure illustrated in FIG. 17 has a clip form factor.

FIGS. 3A-3B, 4A-4D, 5A-5B, 6, 7A-7C, 9A-9D, 12A, 12C-12D, 15A-15C are other views of the ring assembly or portions thereof.

As shown in FIG. 2A, laser 160 of optical blood motion sensor 180 illuminates skin of the user's finger so that light reflected by the skin of the illuminated finger is received by light detector 170. In the particular example of FIG. 2A, both laser 160 and light detector 170 are facing inwards (i.e. towards the finger in this case) and are mounted to an outward-facing surface of the ring assembly. The ring assembly includes an inflatable cushion (not explicitly labelled and/or shown in FIG. 2A) having a barrier for providing a gas-seal between an interior of the cushion 120 and locations outside of the cushion. The barrier has a portion (not shown in FIG. 2A) that is flexible and optically-transparent (FOT) which applies inwardly pressure (e.g. at least systolic pressure) upon the finger of the subject.

Pressurized fluid (e.g. pressurized gas or pressurized liquid) is forced through tube 124 to inflate the cushion and to apply pressure (e.g. inwardly-directed) on the biological tissue (e.g. finger).

When the cushion (e.g. 120) is inflated (i.e. at least partially inflated) (e.g. via tube 124) so that a portion of a flexible barrier (e.g. a FOT barrier portion) (e.g. a portion of inner ring 104) inwardly applies pressure upon the user's finger: (i) laser 160 illuminates the user's biological tissue (i.e. skin of the finger in this example) with laser light that is scattered and/or reflected by the biological tissue; (ii) laser light scattered and/or reflected by the biological tissue is received by light detector 170. As will be discussed elsewhere, in embodiments of the invention, en route from laser 160 to the biological tissue the laser light traverses the pressure-applying cushion and/or an interior of the cushion and/or an optically-transparent region of a rigid restrictor (discussed below). As will be discussed elsewhere, in embodiments of the invention, en route from the illuminated biological tissue to light detector 170 the reflected and/or scattered laser light traverses the pressure-applying cushion and/or an interior of the cushion and/or an optically-transparent region of a rigid restrictor (discussed below).

As shown in FIGS. 2A-2B, the system for optically measuring systolic and/or diastolic blood pressure further comprises blood motion computation circuitry 102 for computing, from laser light reflected by the biological tissue (e.g. finger) and received by light detector 170 a blood-motion signal descriptive of arterial blood motion (e.g. a pulsatile signal). Blood motion computation circuitry 102 may be implemented by any combination of software, hardware (e.g. digital and/or analog) and firmware.

As shown in FIG. 2B, collectively, the combination of laser 160, light detector 170 and blood motion computation circuitry 102 comprise an optical blood motion sensor 180. Examples of optical blood motion sensors include laser Doppler sensors, DLS sensors and PPG sensors.

The system for optically measuring systolic and/or diastolic blood pressure further comprises blood pressure circuitry 104 (e.g. implemented by any combination of software, hardware (e.g. digital and/or analog) and firmware) for computing a systolic and/or diastolic blood pressure, from the combination of (i) output of the optical blood motion sensor (e.g. a pulsatile signal computed by the blood motion sensor) and (ii) a measurement of pressure applied by the inflatable cushion or cuff upon the biological tissue (e.g. skin of the finger). —for example, from a time-correlation between the optical blood motion sensor and the pressure measurement.

In some embodiments, the pressure applied by the inflatable cushion or cuff upon the biological tissue (e.g. by FOT barrier portion thereof of the cushion) may be measured according to a measurement of an internal pressure inside the inflatable cushion. Towards this end, structures where the blood motion sensor 180 is situated to avoid mechanical interference (i.e. non-contact configuration—for example, sensor 180 and tissue 159 are on opposite sides of a rigid restrictor) may be preferred since for these structures the internal pressure inside the inflatable cushion would more accurately matches the pressure applied by the inflatable cushion or cuff upon the biological tissue.

Although it may be preferred to measure applied pressure by measuring the internal gas or internal liquid pressure (i.e. pressure of gas or liquid disposed within the cushion) within the cushion 120, this not a requirement. Alternatively, this measurement of pressure applied upon the biological tissue by the inflatable cushion (e.g. by FOT barrier portion thereof) may be obtained directly—e.g. by measuring directly force applied on the surface of the biological tissue using, for example, using a strain gauge and dividing this measured force by an applied area.

Figure 13:
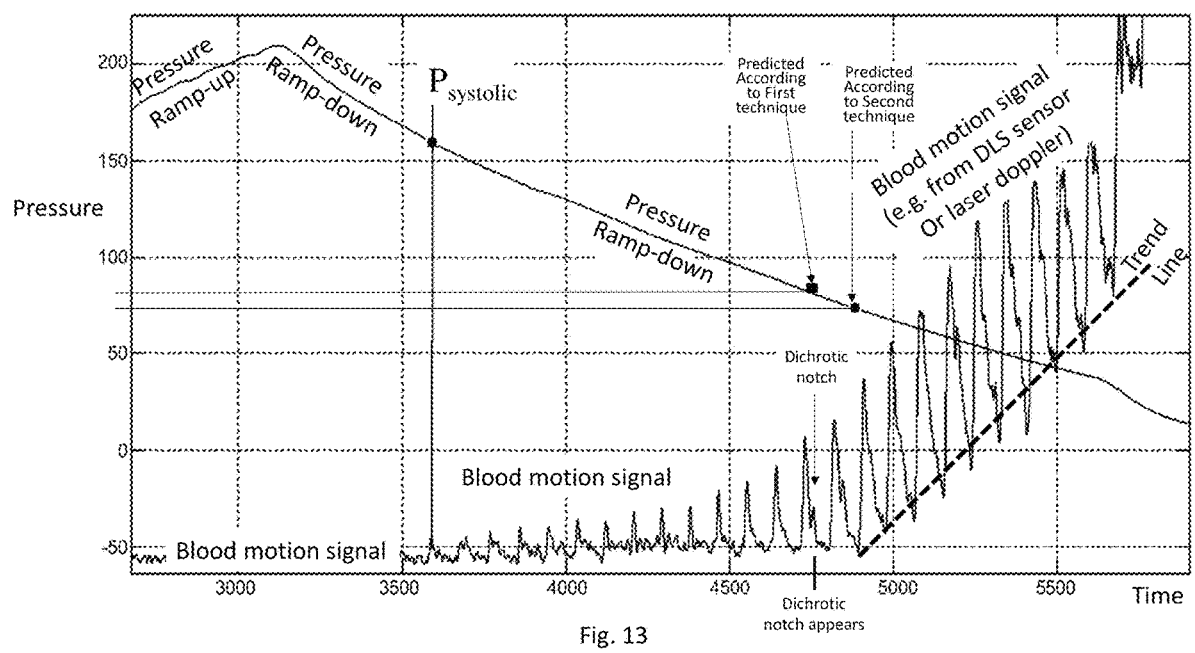
FIGS. 13-14 illustrate a blood motion signal as a function of time.
Figure 14:
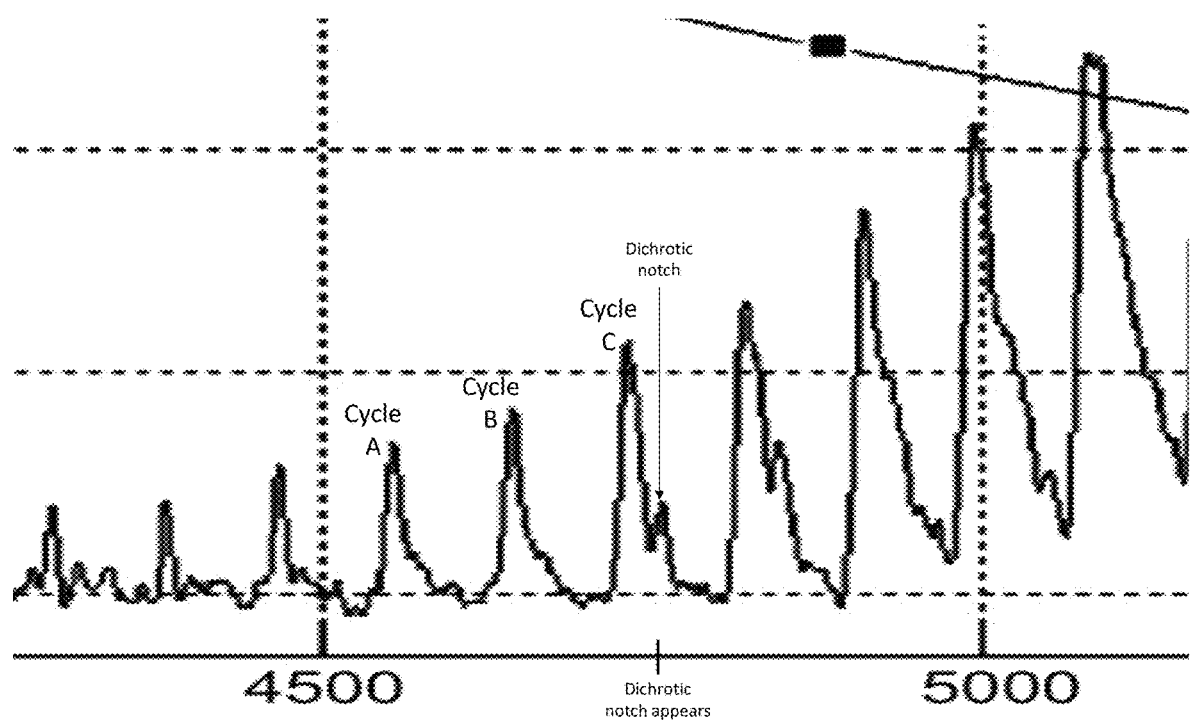

As noted above, the system comprises arterial blood pressure circuitry 104—in one particular non-limiting embodiment, blood pressure circuitry 104 optionally operates according to the procedure disclosed with reference to FIGS. 13-14. For example, blood pressure circuitry 104 may optionally include pulse-wave-form (PWF) scoring engine 156.

Figure 2C:
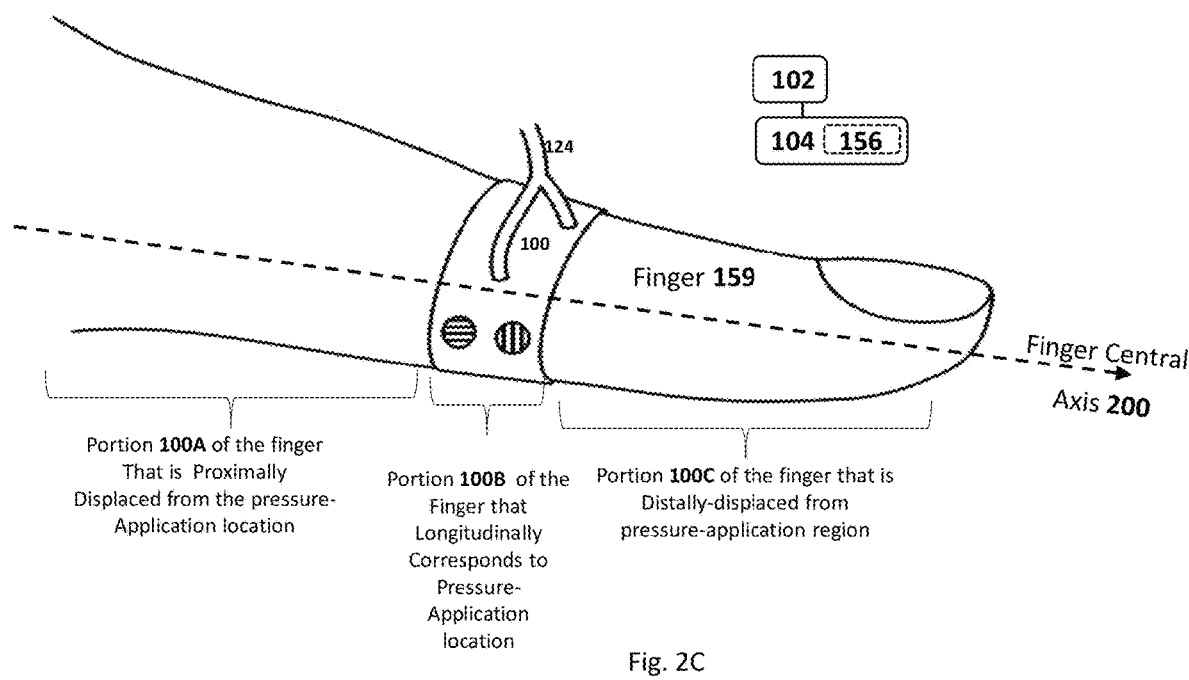

FIG. 2C is in contrast to the example of FIG. 1. As shown in FIG. 2C, the optical measurement of blood motion may be performed on a portion 100B of the finger that longitudinally (i.e. along a finger central axis 200) corresponds to a pressure-applying location. In contrast, in the example of FIG. 1, the optical measurement of blood motion is performed on a portion 100B of the finger is distally displaced from pressure-applying location. Not wishing to be bound by theory, it is believed that this allows for a more accurate measurement of systolic and/or diastolic blood pressure since the biological tissue is optically probed at a location where the physiological conditions inducted by mechanical pressure (i.e. by inflatable cuff and/or cushion) upon the biological surface prevail.

Also shown in FIG. 2A is portion 100A of the finger is proximally displaced from pressure-applying location.

FIG. 3A is another illustration of ring assembly 100. FIG. 3B is a cross-section. As shown in FIG. 3B, the ring assembly 100 includes nested inner 104 and outer 108 rings (e.g. having a common centroid 158) disposed around a central axis, 298 (e.g. centroid 158 is on central axis 298) the inner ring 104 comprising a section that is flexible and optically-transparent (FOT), the outer ring 108 comprising a rigid section The outer 108 and inner 104 rings defining the following three regions: i. an innermost region 168 within the inside of the inner ring 104 (e.g. through which the user's finger passes—e.g. substantially aligned with axis 298); ii. an annular-shaped mediating region 188 outside of the inner ring 104 and within the outer ring 108 (e.g. where an interior of a gas-sealed inflatable cushion and/or chamber is disposed); iii. an outermost region 198 exterior to the outer ring 108 (e.g. where at least a portion of blood motion sensor 180 is located—e.g. at least laser 160 and/or detector 170).

Outer Ring 108—in some embodiments, at least a portion of the outer ring 108 is rigid. In embodiments of the invention, this outer ring portion function as a restrictor which decreases an amount of time required to inflate an inflatable chamber and/or cushion (not shown explicitly in FIG. 4B) to at least systolic pressure. In some embodiments, a presence of the restrictor (i.e. at least a portion of the outer ring 108 is rigid) is useful or applying a uniform pressure around a circumference of the user's finger. For example, in some embodiments, outer ring 108 comprises one or more of the rigid section(s) which collectively span at least 180 degrees or at least 270 degrees or at least 315 degrees or 330 degrees around the central axis 298. Although outer ring 108 is drawn as a single section over 360 degrees, it is appreciated that is may be composed of multiple sections and does not need to be 'complete' over the entire 360 degrees.

In various embodiments set forth below, an example will be described where an entirety of the outer ring 108 is rigid. However, this is not a requirement. Although this is not a requirement, providing an outer ring 108 that is entirely rigid may be useful for applying a uniform pressure around the circumference of the finger and/or for minimizing an amount of time required to inflate cushion and/or chamber to inwardly (e.g. from inner ringer 104) systolic pressure upon the finger disposed in innermost region 168.

Inner ring 104—in some embodiments, at least a portion (e.g. an entirety of) of the inner ring 104 is flexible (e.g. some or all of the inner ring is flexible and optically-transparent (FOT)). For example, interior(s) of one or more gas-sealed inflatable chamber(s) or cushion(s) 120 (not shown in FIG. 3B) may be disposed in mediating region 188, and the at least a portion of the inner ring may be a portion of a sealing barrier of the inflatable chamber or cushion in mediating region 188. When the chamber(s) or cushion(s) is inflated, the flexible (e.g. FOT) section of the inner ring applies inwardly-directed pressure upon biological tissue (e.g. finger) disposed in the innermost region 168. Although inner ring 104 is drawn as a single section over 360 degrees, it is appreciated that is may be composed of multiple sections and does not need to be 'complete' over the entire 360 degrees.

Thus, in different embodiments at least a portion of inner ring 104 is flexible and transparent (FOT). In various embodiments set forth below, an example will be described where an entirety of the inner ring 104 is flexible and/or optically transparent. However, this is not a requirement—see FIG. 8A. Although this is not a requirement, providing an inner ring 104 that is entirely flexible may be useful for applying a uniform pressure around the circumference of the finger.

Figures 4A, 4B:
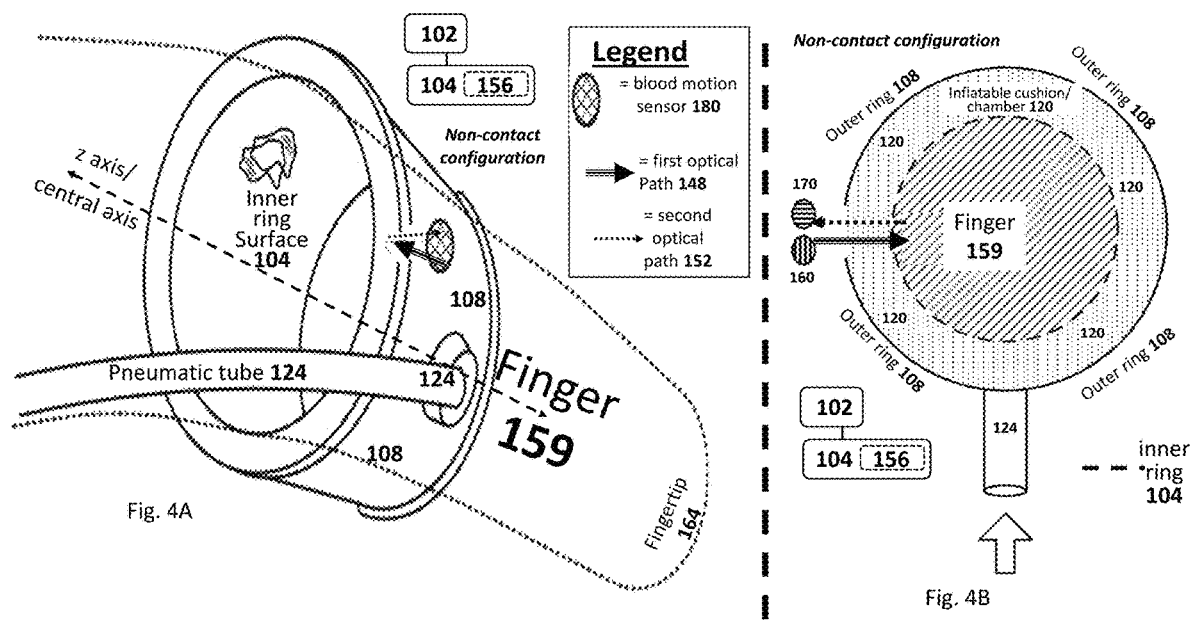

Mediating region 188—in embodiments of the invention, respective interiors of one or more a gas-sealable inflatable chambers is(are) disposed in the mediating region between the FOT section of the inner ring and the rigid section of the outer ring (e.g. to collectively span at least 180 degrees or at least 270 degrees or at least 315 degrees or 330 degrees around the central axis 298). In the example of FIG. 4B, a single inflatable chamber 120 occupies an entirety of mediating region 188. In the example of FIG. 4D, multiple inflatable chambers 120A, 120B supplied with pressurized gas (or liquid) by tubes 124A, 124B are shown.

FIGS. 4A-4D—As shown in FIG. 4B, when air is forced into chamber 120 via conduit 124, this forces inward motion of at least a portion of inner ring 204 (e.g. that is a FOT surface of a barrier portion of a cushion and/or chamber 120 within mediating region 188). This causes the FOT surface to apply inward pressure upon biological tissue 124 (e.g. a finger) disposed within region 168.

FIGS. 4B-4D and 5A-5B, 6, 7A-7C, 8, 9A-9D, 12A and 12C-12D illustrate illumination of finger 159 (i.e. disposed in innermost region 168) at a time when inflatable cushion/chamber 120 is at least partially inflated (e.g. from tube 124) to apply inward pressure (e.g. at least systolic pressure) upon the finger.

At this time, laser 160 (e.g. VCSEL) and photodetector 170 of blood motion sensor 180 operate. As will be discussed elsewhere, in different embodiments, blood motion sensor 180 may be a laser Doppler sensor, a dynamic light scattering (DLS) sensor, or a pulse sensor.

In different embodiments and as shown in FIG. 4B and in other figures, (i) no direct contact is required between the laser light source 160 which illuminates the tissue and the skin of the subject (e.g. skin of finger 124) and/or (ii) no direct contact is required between the light detector 170 which receives light reflected and the skin of the subject. Thus, there may be a 'gap' between the light source and the skin of at least 1 mm or at least 3 mm or at least 5 mm—within this gap is material (i.e. solid, liquid or gas) that is transparent to at least a portion of the visible and/or IR spectrum (i.e. to a wavelength of the light source).

In the example of FIGS. 2A-2C, 3A-3B, 4A-4D, 5A-5B, 6, 7A-7C, 9A-9B, 12A, 12C-12D, and 15A, it is possible to locate the light source(s) and/or light detector 170 on a 'outer surface' of outer ring 108 which faces outward and/or away from the subject's skin (and from the innermost region 168) Alternatively or additionally (NOT SHOWN), it is possible to locate light source(s) and/or light detector in an interior of an inflatable chamber 120 which applies inward pressure on finger 124. Alternatively or additionally (NOT SHOWN), it is possible to locate light source(s) and/or light detector interior to outer ring 108 but outside of chamber 120—see, for example, FIGS. 9C-9D.

Figure 5A:
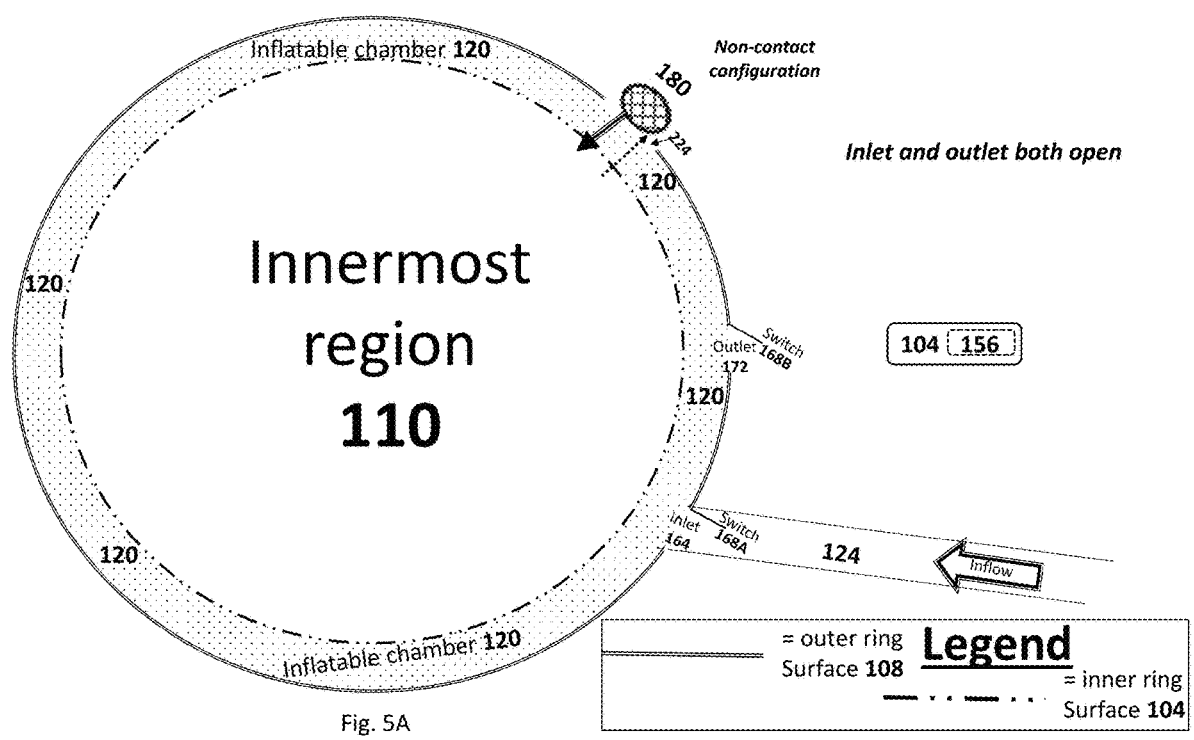

Introduction of pressurized gas (e.g. air) or liquid into chamber 120 (e.g. via pneumatic tube 124 illustrated in FIG. 4A—for example, a pneumatic pump (NOT SHOWN) forces air into chamber 120 via inlet 164 of FIG. 5A) into air-tight inflatable chamber 120 inflates air-tight inflatable chamber 120. Inflation of the inflatable chamber 120 serves to apply the pressure upon the biological tissue (e.g. finger) in annulus-internal region 110—for example, an FOT portion of inner ring 104 applies the inward pressure on finger 124.

In one example, outer ring surface 108 (or at least a portion thereof—e.g. at least 180 degrees around central axis 298) is rigid and the inner surface 104 (or at least apportion thereof) is flexible—thus, inflation of the chamber 120 causes inward movement (i.e. into and at the expense of annulus-internal region 110) of inner surface 104 while outer ring surface 108 maintains its dimensions—i.e. introduction of pressurized gas or liquid into chamber 120 does not deform outer ring surface). This combination facilitates application of inwardly-directly pressure that is relatively uniform around the ring. In addition, because the outward ring surface 108 maintains its dimensions, this may be useful for maximizing the inward movement and/or pressure applied upon the biological tissue in annulus-internal region 110 for a given quantity of pressurized gas (e.g. air) or liquid introduced into chamber 120.

In the examples, an inside of pneumatic tube 124 in fluid communication with an interior of chamber 120.

In some embodiments, annular shaped ring assembly 100 provides the following features: (i) at least a portion of the outer 108 surface is optically transparent to at least a portion of the visible and/or IR/or NIR spectra and (ii) at least a portion of the inner 104 surfaces is optically transparent to at least a portion of the visible and/or IR/or NIR spectra. As such and as illustrated in FIG. 104B, there is: (i) a first optical path 148 between the annulus-internal region 110 and the coherent light source (e.g. VCSEL) of optical sensor 140 via the outer and inner ring surface that is transparent to the portion of the visible and/or IR spectra—i.e. the entirety of the first optical path 148 passes through air (e.g. pressurized air within chamber 120) or through material that is transparent to the portion of the visible and/or IR spectra; (ii) a second optical path 152 between the annulus-internal region 110 and the light detector source (e.g. VCSEL) of optical sensor 140 via the outer and inner ring surface that is transparent to the portion of the visible and/or IR spectra—i.e. the entirety of the second optical path 152 passes through air (e.g. pressurized air within chamber 120) or through material that is transparent to the portion of the visible and/or IR spectra.

Figures 5B, 106B:
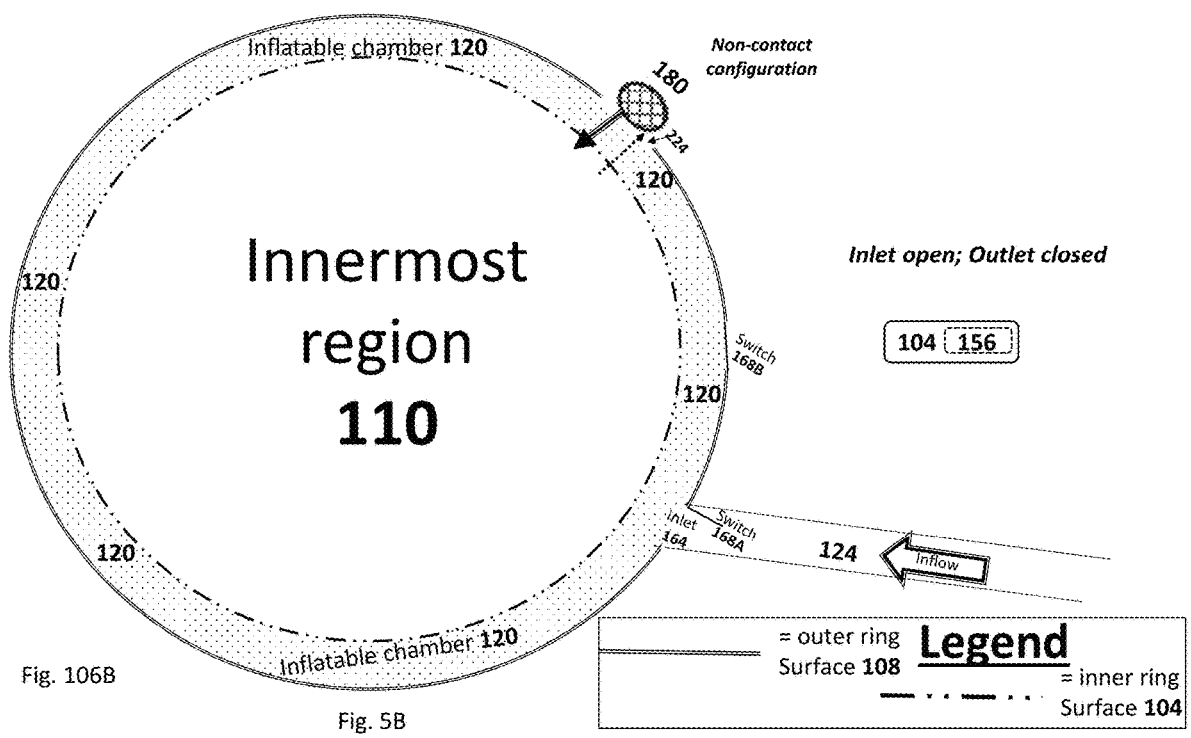

Illustrated in FIG. 5A-5B is (i) reversibly openable and reversibly closable inlet 164 via which pressurized gas (e.g. air) or liquid is forced into chamber 120 (e.g. via tube 124); (ii) reversibly openable and reversibly closable outlet 172 via which the gas or liquid leaves chamber 120. This allows for a 'ramp up' and a 'ramp down' of pressure—e.g. electronic element(s) controls the degree to which inlet 164 is open or closed (e.g. by regulating a position of switch 168A) and/or electronic element(s) controls the degree to which outlet 172 is open or closed (e.g. by regulating a position of switch 168B).

Figure 6:
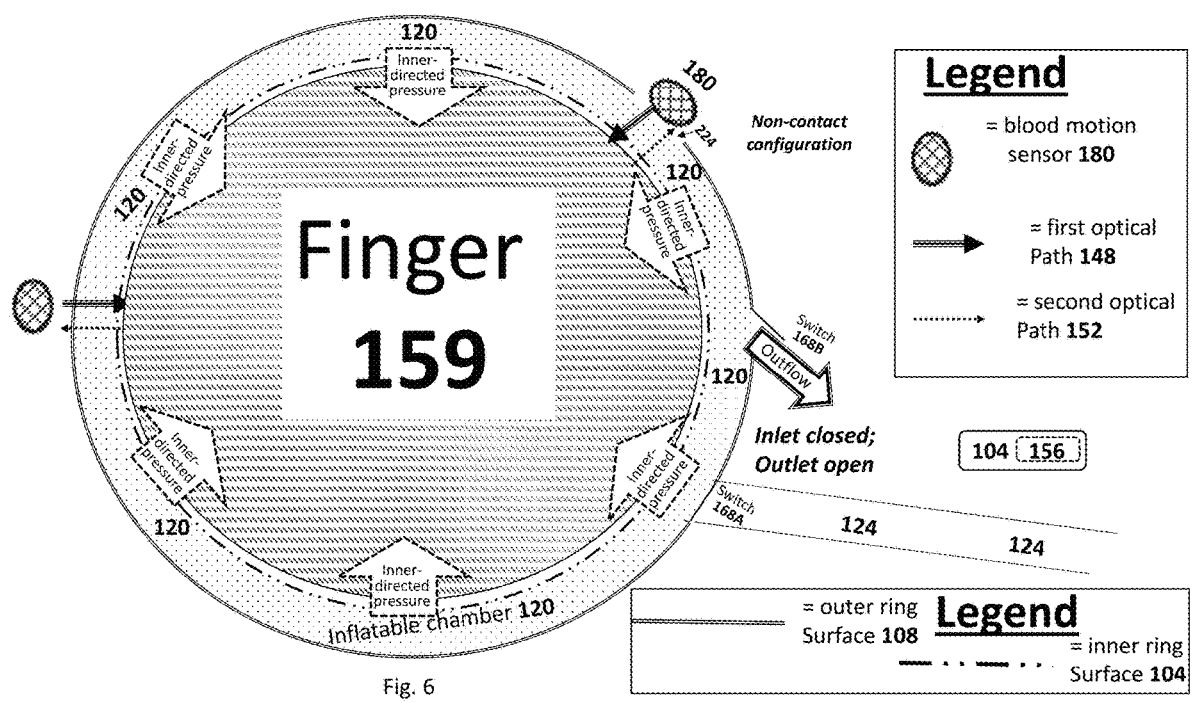

FIG. 6 illustrates an embodiment with multiple blood motion sensors 180—for example, their signals may be averaged for a more accurate measurement.

Figure 7A:
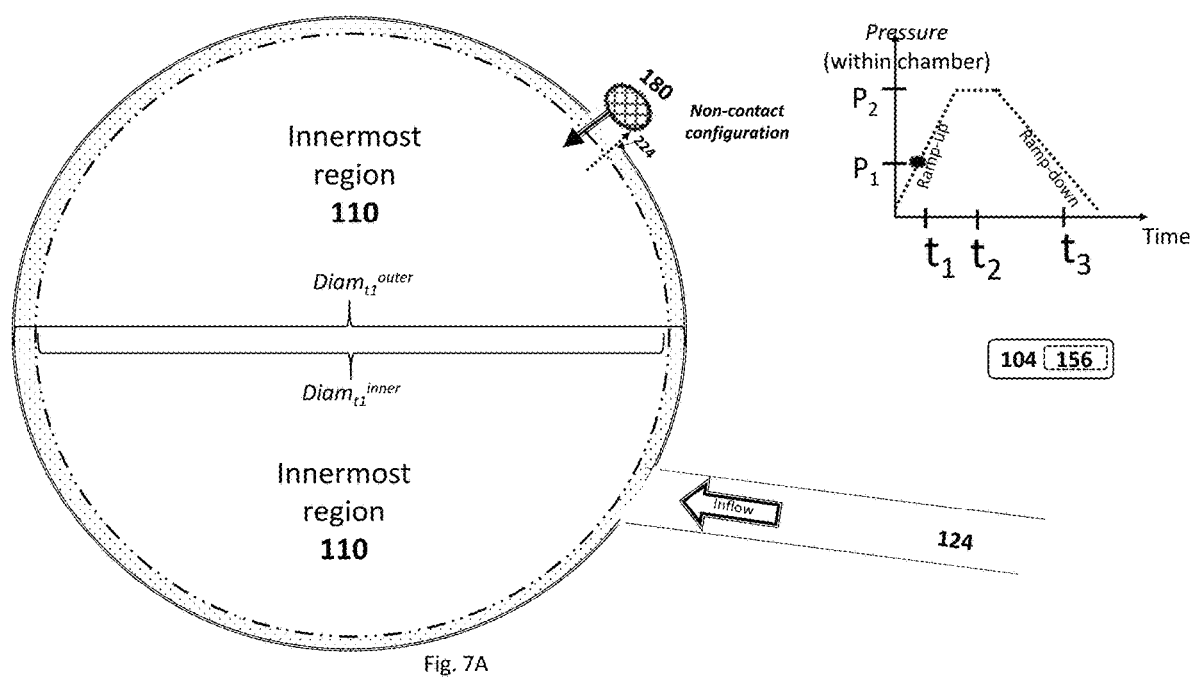
Figure 7B:
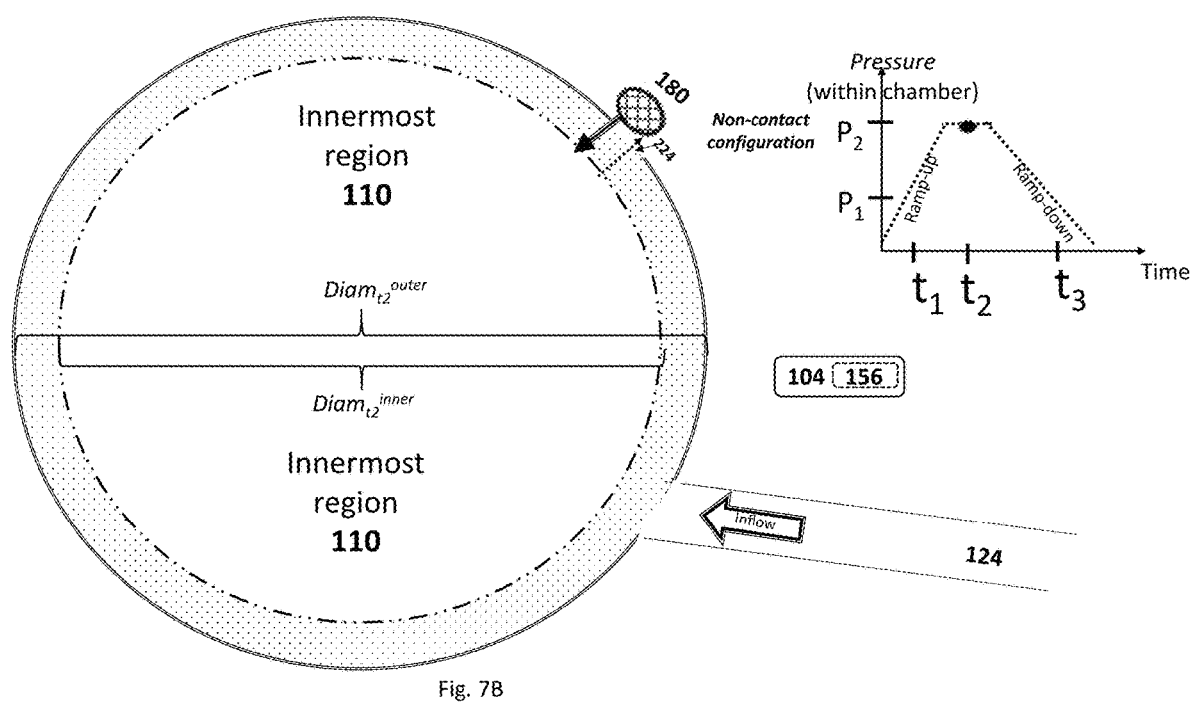
Figure 7C:
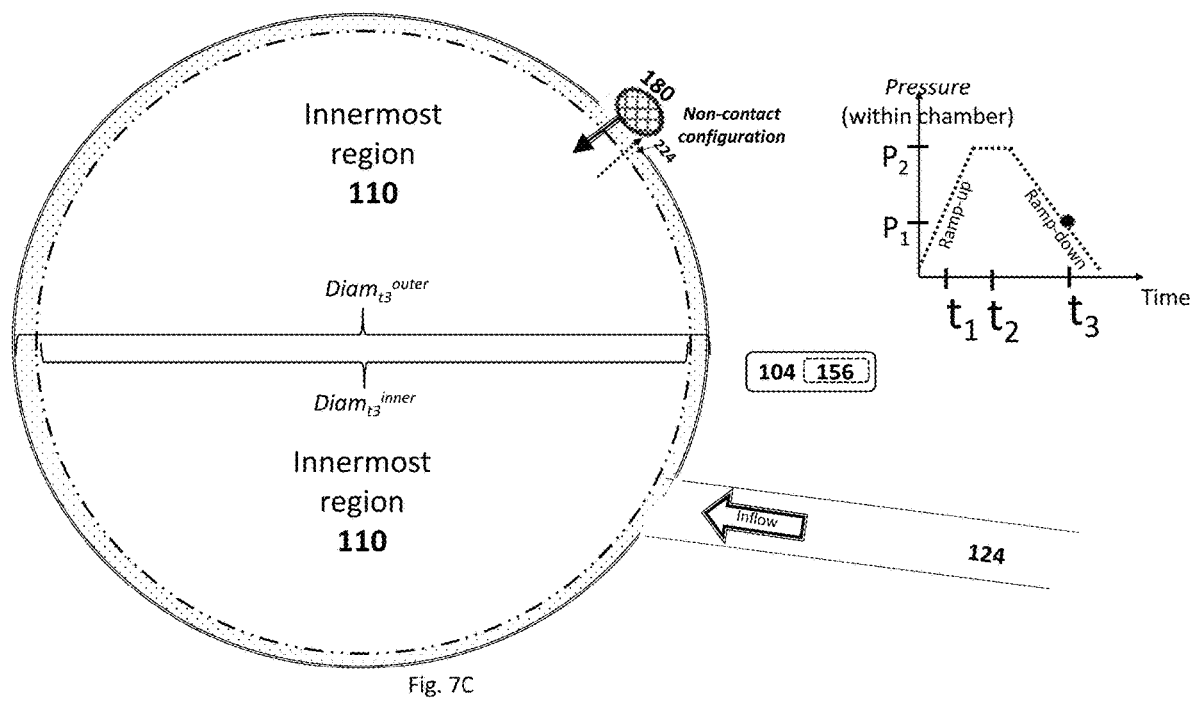

FIG. 7A-7C illustrate pressure ramp-up over time—at time t1 the pressure is relatively low at P1; over time, pressurized gas (e.g. air) or liquid is introduced (e.g. by pump (NOT SHOWN) via 124) to ramp up the pressure to P2 at time t2—e.g. switch 168A keeps inlet open and/or switch 168B keeps outlet 172 closed. After the pressure increases to P2, outlet 172 is opened to ramp down the pressure within chamber 120.

Figure 8A:
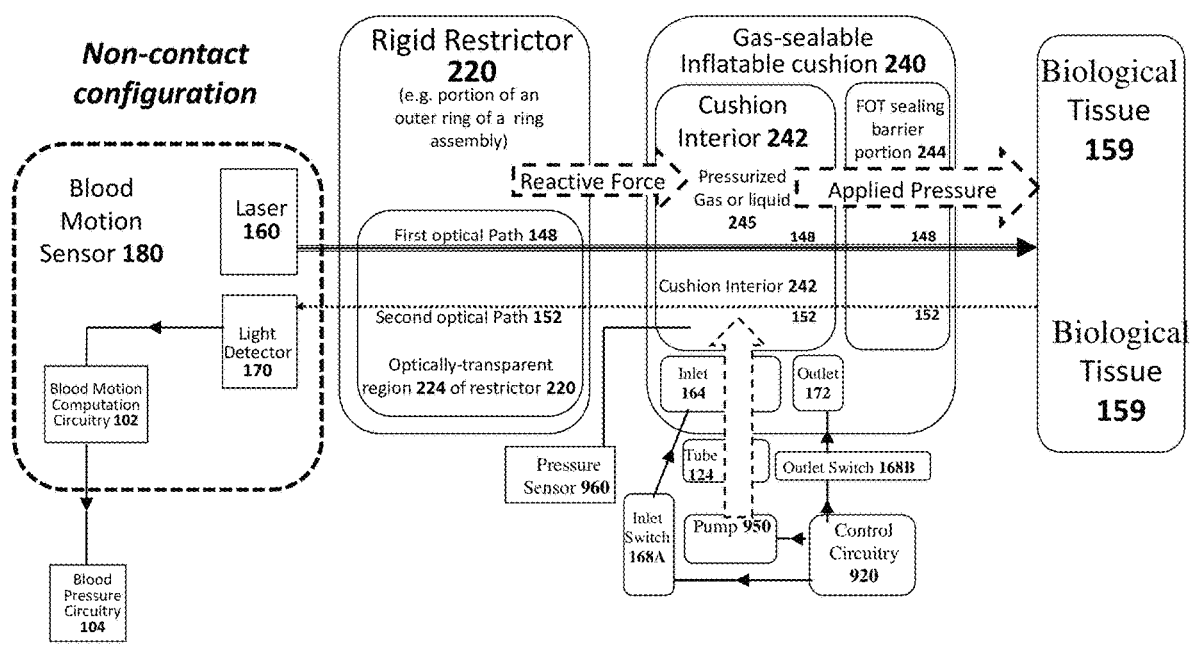

FIG. 8A is a block diagram comprising: (i) an optical blood motion sensor 180; (ii) a rigid restrictor 220 (e.g. provided as a portion or an entirety of outer ring 108) comprising optically-transparent region 224; (iii) one or more gas-sealable inflatable cushion(s) 240 (e.g. disposed in mediating region 188 between outer 108 and inner 104 rings—e.g. chamber 120); and (iv) biological tissue Innermost region 168. Cushion 240 includes a cushion interior 242 where pressurized gas 245 (or liquid) is disposed (e.g. after entering via intel 268A and tube 124) As shown in FIG. 8A, this pressurized gas (or liquid) applies pressure upon tissue 159 via FOT barrier portion 244 (e.g. at least a portion of inner ring 104 as in FIG. 8B).

Figure 8B:
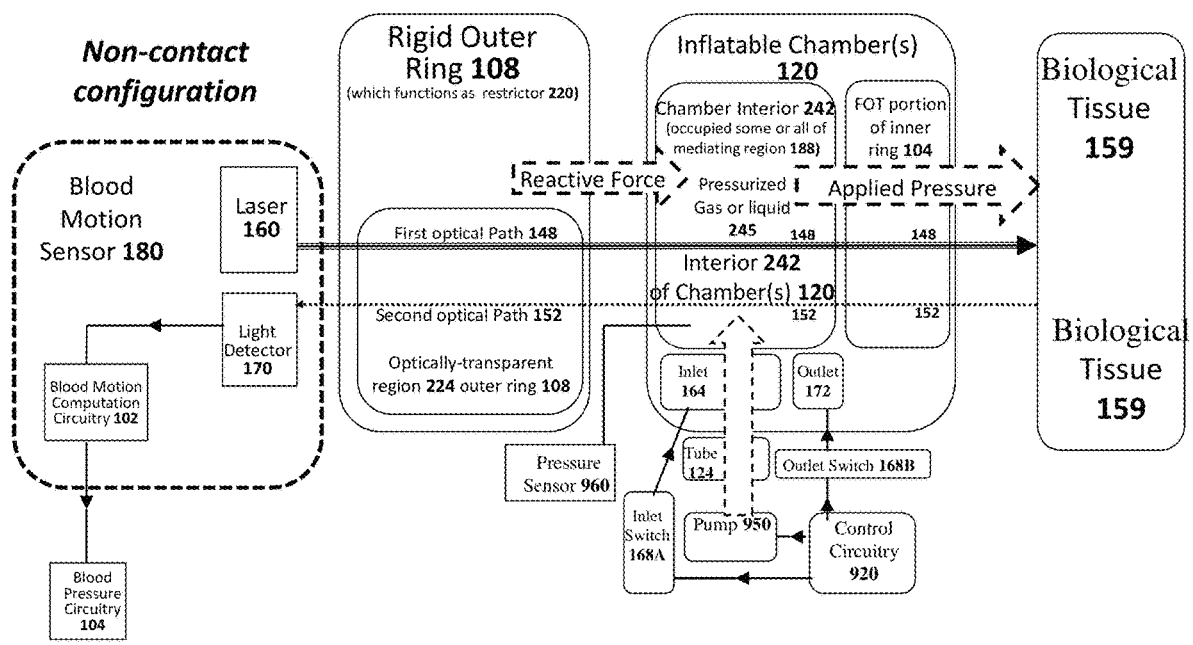

FIG. 8B is implemented according a 'ring assembly form factor' while FIG. 8A relates to the more general case.

In some 'ring assembly' embodiments (e.g. FIG. 8B), (i) locations of the outer ring spanning 360 degrees around central axis 298 are rigid, and at least a portion of that 224 is optically transparent (i.e. void in outer ring 108 or a portion of outer ring 108 constructed of material that is optically transparent); (ii) locations of inner ring 104 spanning around central axis 298 are flexible; (iii) at locations of optical path 148 and 152 inner ring 104 is optically transparent; (iv) locations of mediating region spanning 360 degrees around central axis 298 and spanning the radii between that of the inner ring 104 and that of the outer ring 108 are occupied by a single inflatable chamber 120 or cushion; (v) FOT portions of inner ring 104 serve as a gas-sealing barrier of the inflatable chamber 120 of cushion and are forced inwards upon inflation of the chamber of cushion 120.

Figure 12B:
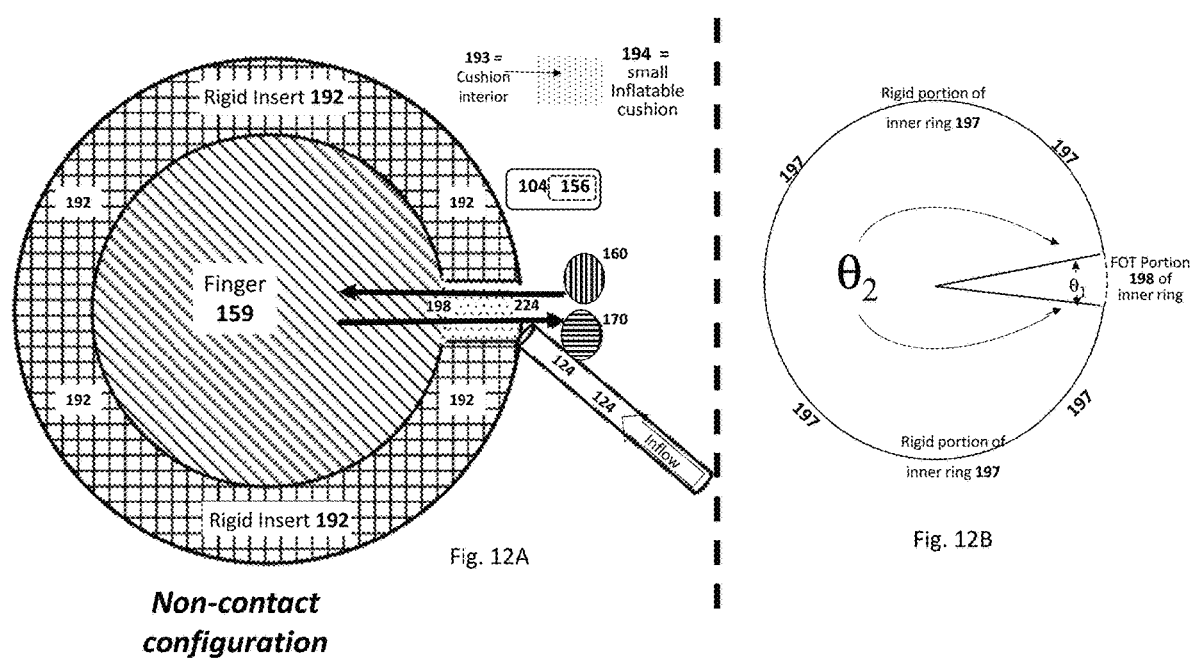

In alternative embodiments different from FIG. 8B, FIG. 8A is implemented according to features of FIGS. 12A-12B (discussed below) or features of FIG. 17 (clip form-factor).

As shown in FIG. 8A laser light from laser 160 follows a first optical path 148 through the optically-transparent region 224 of restrictor 220. Restrictor 220 may be implemented at 360 degrees of outer ring 20 (which is all rigid around 360 degrees) as in FIGS. 3-7, wherein at least portion of the outer ring is optically-transparent region 224. Although not required, this may be preferably for providing uniform pressure around the circumference of the finger, but it not required.

As shown in FIG. 8A, first optical path 148 also passes through FOT sealing barrier portion 244 of gas-sealable inflatable cushion 240 as well as cushion interior 242 (e.g. in mediating region 188 for ring-assembly embodiments). For example, as is FIGS. 3-7, 360 degrees of inner ring 104 may be a flexible (but not necessarily optically-transparent) and serve as a gas-sealing barrier of an annular shaped cushion or chamber 120.

FIGS. 12A-12D relates to alternative embodiments and are discussed below

As shown in FIG. 8A-8B, in some embodiments the air-tight inflatable cushion 240 or chamber 120 has an inlet 164 and an outlet 172. Also shown is (i) a pneumatic tube 124 in fluid communication with an inside 242 of the air-tight internal chamber via the inlet; c. a pneumatic pump 950 to inflate the internal air-tight chamber 120 via the pneumatic tube 124 and the inlet 164 so as to cause inward and deforming movement of flexible inner ring surface while the rigid outer ring surface retains its dimensions and shape; d. an electrically controlled inlet switch 168A for opening and closing the inlet 164; e. an electrically controlled outlet switch 168B for opening and closing the outlet 172; f. pump control circuitry 920 configured to: i. cause the pneumatic pump to inflate the air-tight inflatable chamber, thereby ramping up a magnitude inward-directed pressure applied by the inner ring surface upon annulus-internal-region-disposed-biological tissue; and ii. causing the outlet switch to open the outlet so as to drain air from the air-tight inflatable chamber, thereby ramping down a magnitude of the inward-directed pressure applied by the inner ring surface upon the annulus-internal-region-disposed-biological tissue; g. a pressure sensor 960 for sensing and/or measuring a pressure inside of the air-tight inflatable chamber and/or a pressure sensor for sensing and/or measuring a pressure inside of pneumatic tube 124.

Blood pressure circuitry 970 computes a blood systolic and/or diastolic blood pressure of the biological tissue by correlating output of the pressure sensor 960 with output (i.e. the results of 'optically sensing pulse' or blood flow) of the optical blood motion sensor 108.

Figure 9A:
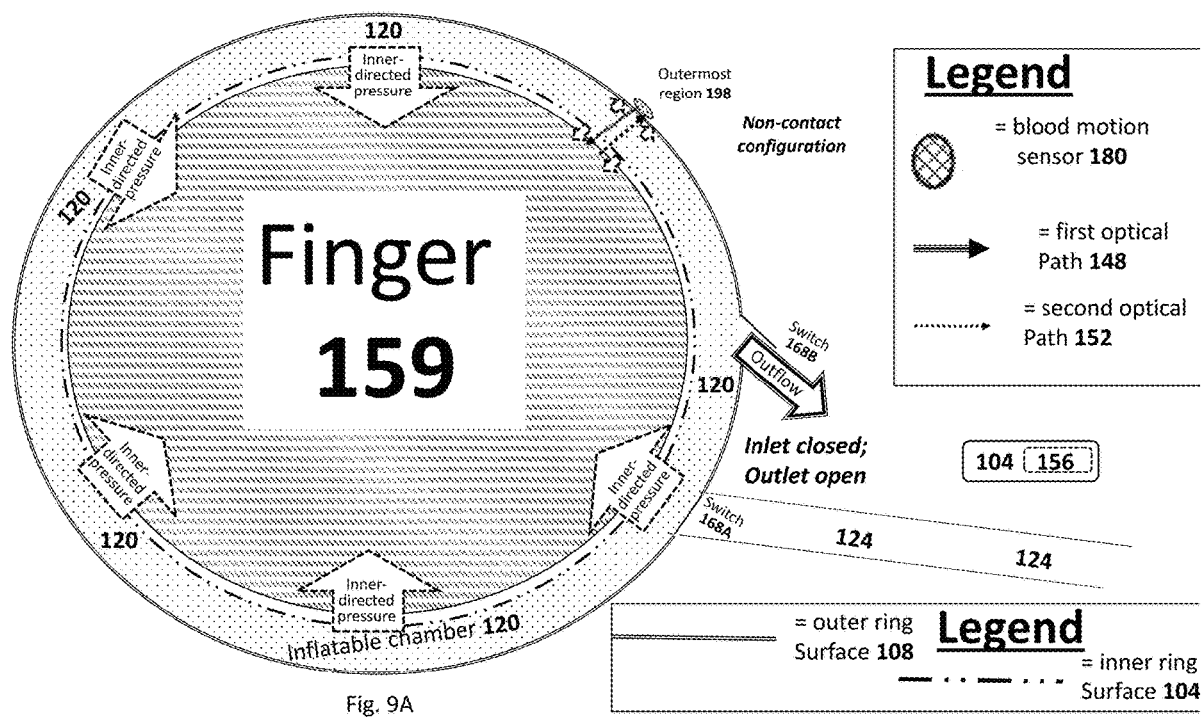
Figure 9B:
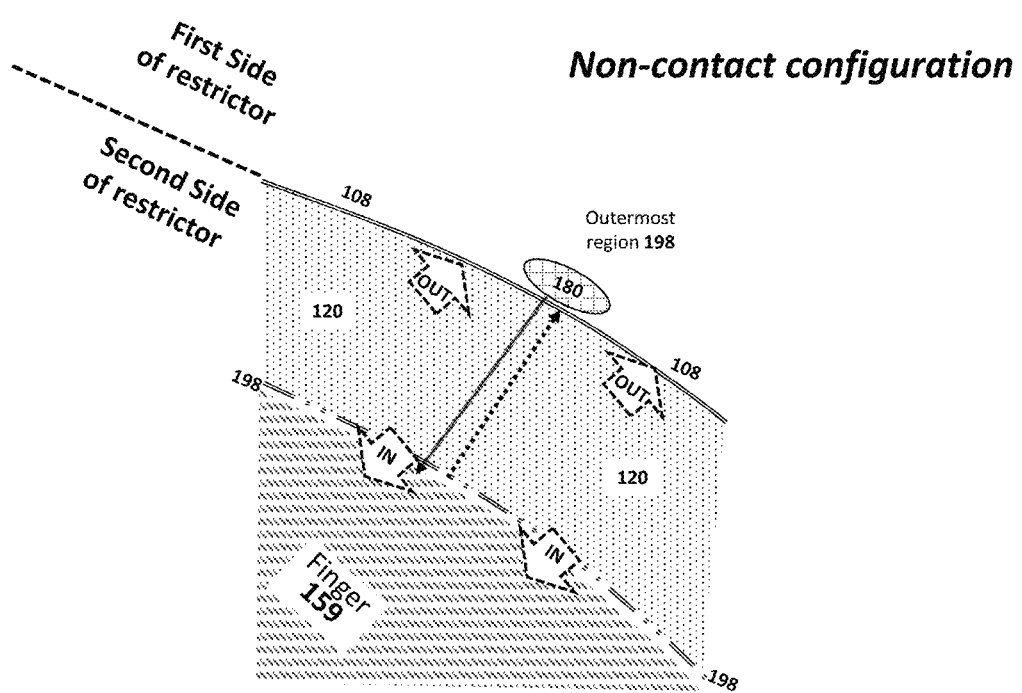
Figure 9C:
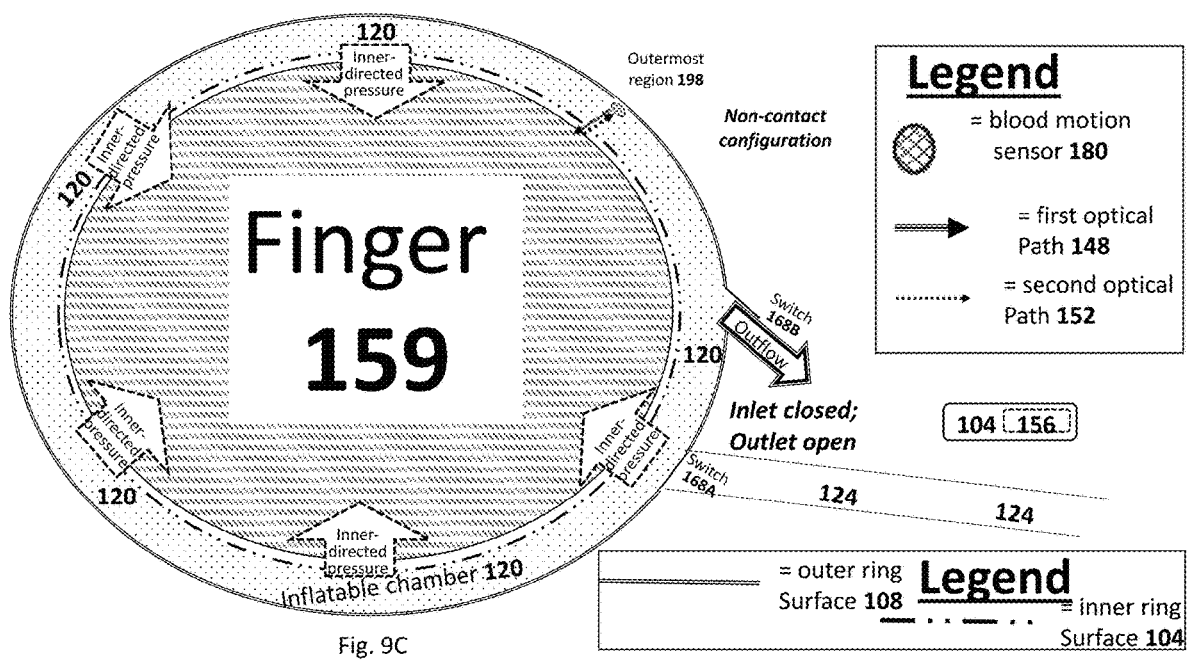
Figure 9D:
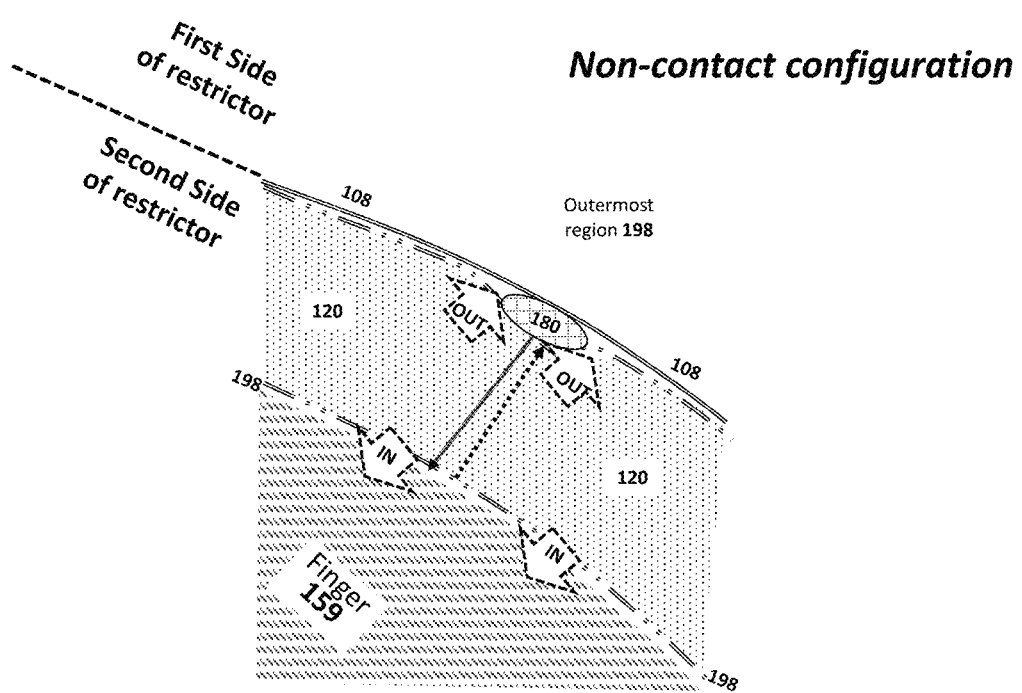

Reference is now made to FIGS. 9A-9B. In embodiments when a rigid restrictor (e.g. at least a portion of outer ring 108) is used, disposing the biological tissue and the laser on the same side of the restrictor (see FIGS. 9C-9D where both sensor 108 and tissue 159 are on the 'second ride' of the restrictor—i.e. both are within outer ring 108) might lead a situation where a presence of laser (or other parts of the optical blood motion sensor 108) causes 'mechanical interference'—i.e. either uneven application or pressure or a situation where the gas pressure (or pressure of liquid) inside of the cushion does not accurately reflect a magnitude of the pressure applied to the surface.

As such, instead of disposing the biological tissue and the laser on the same side of the restrictor, according to embodiments of the invention, it is preferred to dispose the laser either within inside of the rigid restrictor (e.g. embedded inside) or such (e.g. see FIGS. 9A-9B along with FIGS. 4B-4D and 6) that laser and the biological tissue are disposed on opposite sides of the rigid restrictor (e.g. the tissue within 'within' ring 108 and the laser 160 and/or detector 170 is outside of ring 108). As such and as shown FIG. 8A-8B, the rigid restrictor 220 might require the optically transparent region 224 (e.g. either optically-transparent material or a void or window in restrictor 220) through which laser light passes en route to the biological tissue.

As noted above, a presence of the rigid restrictor 22—serves to reduce the amount of time required to inflate the cushion and/or serves to evenly distribute applied pressure around a circumference of the subject's finger of toe. In some embodiments, (i) blood pressure measurement apparatus comprises a 'ring assembly' cuff assembly ((or ring assembly) having a generally cylindrical shape and disposed around a user's finger or toe; and (ii) the rigid restrictor has a circular shape (or is a rigid portion of an objection that has a circular shape) around the user's finger. In these embodiments, having rigid material at various locations (e.g. all the around) the user's finger is useful for evenly distributing pressure applied to the finger along the finger circumference and/or further reducing the amount of time required to inflate the cushion. In these embodiments, there may be an advantage to a restrictor/ring which is rigid in its entirety—however, even in these embodiments, the present inventors (at present) to do not see any advantage of disadvantage for material of the restrictor to be optically transparent around most or an entire circumference finger—e.g. as long as a region of the rigid restrictor is 'optically transparent.'

In various embodiments (i.e. irrespective of the rigid restrictor), the FOT barrier section (e.g. pressure-applying) and/or an interior of the cushion and/or the optically transparent region of the rigid restrictor serves to provide a gap between (i) the laser of the optical blood motion sensor and (ii) the illuminated biological tissue to prevent contact therebetween. In different embodiments, a thickness of this gap is at least 1 mm or at least 2 mm or at least 3 mm or at least 5 mm.

Discussion of FIGS. 10A-10B

FIG. 10A illustrates a method of optically measuring blood pressure of a mammal—e.g. using apparatus of FIG. 8A.

Step S201 teaches providing S201 a ring assembly 100 comprising nested outer 108 and inner 104 rings disposed around a central axis, the inner ring comprising a section that is flexible and optically-transparent (FOT), the outer ring comprising a rigid section, the outer and inner rings defining the following three regions: i. an innermost region 168 within the inside of the inner ring 104; ii. an annular-shaped mediating region 188 outside of the inner ring 104 and within the outer ring 108; iii. an outermost region 198 exterior to the outer ring 108, an interior of a gas-sealable inflatable chamber 120 being disposed in the mediating region between the FOT section of the inner ring and the rigid section of the outer ring.

Figure 4C:
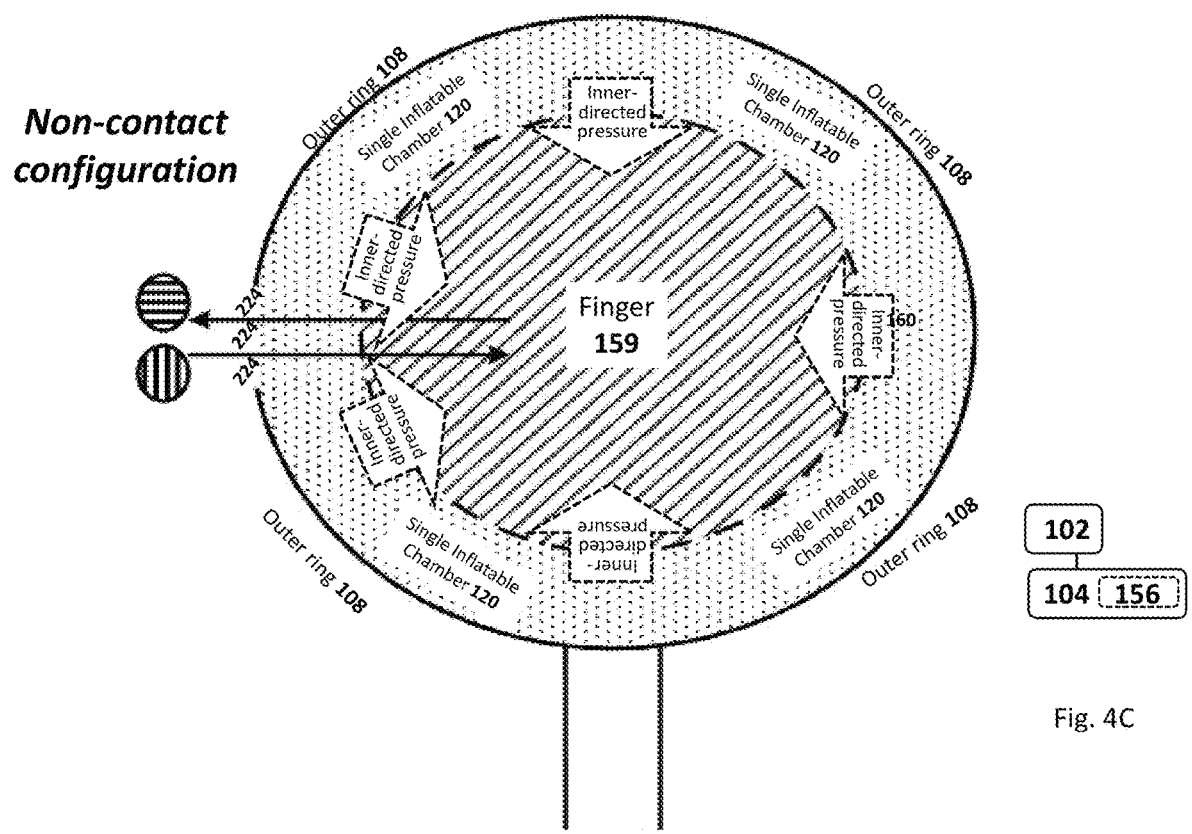
Figure 4D:
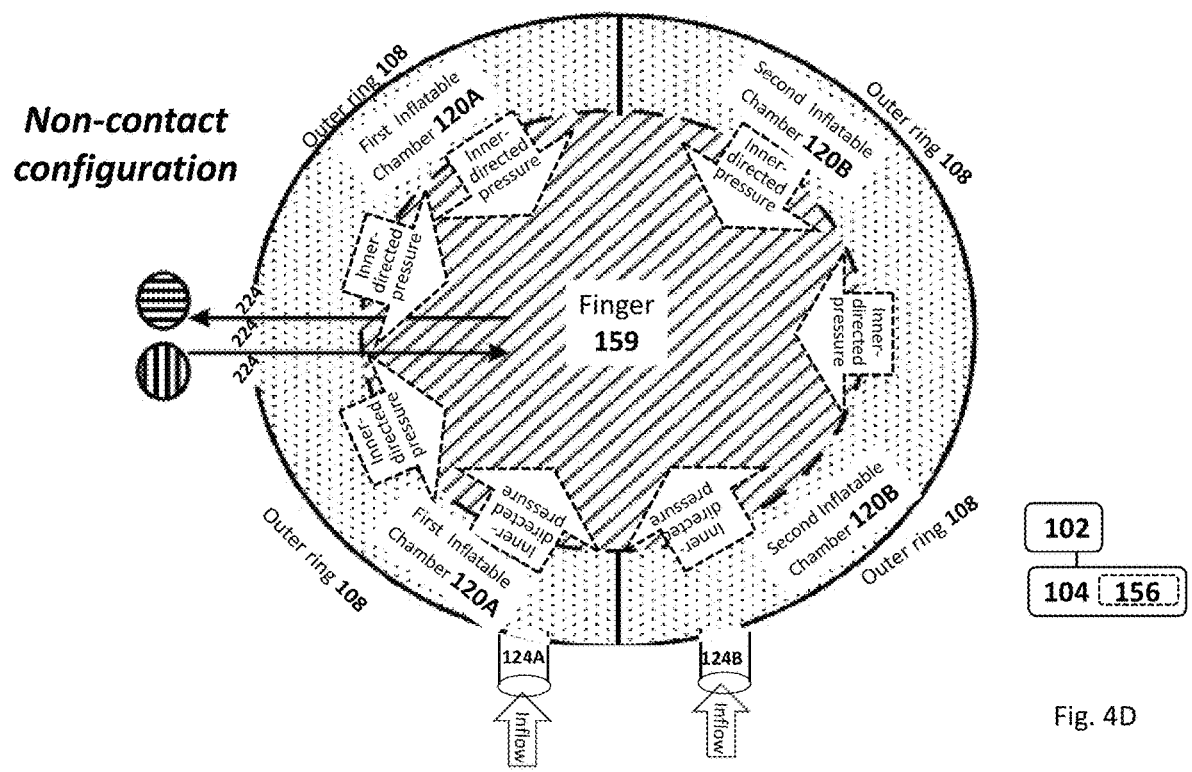

Step S205 teaches the following: when biological tissue 159 is disposed in the innermost region 168, inflating the chamber 120 so as to force the FOT section (i.e. at least a portion of 104—for example, shown in FIG. 9B as 198) of the inner ring 104 to apply an inwardly-directed pressure upon the innermost-region-disposed biological tissue 159 (e.g. the inward pressure is illustrated in FIG. 4C)

Step S209 teaches the following: when the cushion 120 is inflated so that the FOT barrier portion 198 inwardly applies pressure to the biological tissue, operating a laser 160 (e.g. VSCEL) and a light detector 170 so that: i. light emitted by the laser is scattered by the innermost-region-disposed biological tissue after traversing both (i.e. along path 148) the interior 242 of the gas-sealable inflatable chamber and the FOT section of the inner ring; ii. the tissue-scattered laser light is received by the light detector after traversing (i.e. along path 152) both the FOT section of the inner ring and the interior of the gas-sealable inflatable chamber;

Step S213 (e.g. performed by blood motion computation circuitry 102) teaches electronically processing (output of the light detector 170 to compute therefrom a pressure-applied tissue blood motion signal (e.g. see FIG. 13) descriptive of blood motion in the biological tissue when subjected to the inwardly-directed pressure.

Step S217 (e.g. performed by blood pressure circuitry 104) teaches computing a systolic and/or diastolic blood pressure of the mammal by correlating a measurement of a gas pressure or liquid pressure (e.g. output of 960) within the inflatable chamber with the computed pressure-applied tissue blood motion signal.

FIG. 10B illustrates a method of optically measuring blood pressure of a mammal having biological tissue—e.g. using apparatus of FIG. 8A or FIG. 8B. For example, a device having a ring assembly or a device with a clip form factor as in FIG. 17.

Step S301 teaches providing a rigid restrictor 220 (e.g. outer ring 108 or a portion thereof) defining an optically transparent region 224 therein, and an inflatable cushion 240 (e.g. chamber 120), at least a portion 244 of a sealing barrier of the inflatable cushion (e.g. a portion of inner ring 104) being flexible and optically transparent (FOT);

Step S305 teaches forcing the FOT to apply pressure (e.g. inward pressure) to the biological tissue by inflating the inflatable cushion (e.g. via tube 124) so that during inflation of the cushion, a presence of the rigid restrictor 220 restricts a range of motion of gas (or liquid) within the inflated cushion and biases inflation-driven motion of the FOT barrier portion in a direction away from the rigid restrictor.

As shown in FIG. 9A-9D where ring 108 is rigid and is a restrictor, the restrictor 108 restricts a range of motion of gas (or liquid) within the inflated cushion so that the gas (or liquid) cannot move 'outwardly' into outermost region 198. As shown in FIGS. 9A-9D, pressurized gas 245 (or liquid) within an interior cushion 120 exerts outwards and inwards pressure—the outwards pressure is counteracted by restrictor 108. Thus, as pressurized gas (or liquid) is introduced into chamber 120 or any other cushion 240, a presence of restrictor 108 biases inflation-driven motion of the FOT barrier portion in a direction away from the rigid restrictor. In this manner, restrictor 108 functions as a 'contra surface' to the FOT surface (e.g. of inner ring 104) by applying the 'reactive force' (see FIG. 8B from 220 to 240)—this 'contra' or 'reactive force' balances the pressure (i.e. outward pressure in the example of FIGS. 9A-9D labelled as 'out') from the pressurized gas (or liquid).

Step S309 teaches when the cushion is inflated so that the FOT barrier portion applies pressure to the biological tissue, operating a laser 160 (e.g. VCSEL) and a light detector 170 so that: A. light emitted by the laser is scattered by the pressure-applied biological tissue after passing (i.e. along path 148) through the optically transparent region 224 of the rigid restrictor 220, the pressure-applying FOT barrier portion 244 (e.g. a portion of inner ring 104) of the inflated cushion, and the inflated cushion interior 242; B. the tissue-scattered laser light is received by the light detector 170 after passing (i.e. along path 152) through the pressure-applying FOT barrier portion 244 of the inflated cushion 240, the inflated cushion interior and the optically transparent region 224 of the rigid restrictor 220.

Step S313 teaches: electronically processing (e.g. by 102) output of the light detector to compute therefrom a pressure-applied tissue blood motion signal descriptive of blood motion in the biological tissue when subjected to the applied pressure.

Step S317 teaches computing (e.g. by 104) a systolic and/or diastolic blood pressure of the mammal by correlating a measurement of a gas pressure (e.g. output of 960) (or liquid pressure) within the inflated cushion with the computed pressure-applied tissue blood motion signal.

Figure 11A:
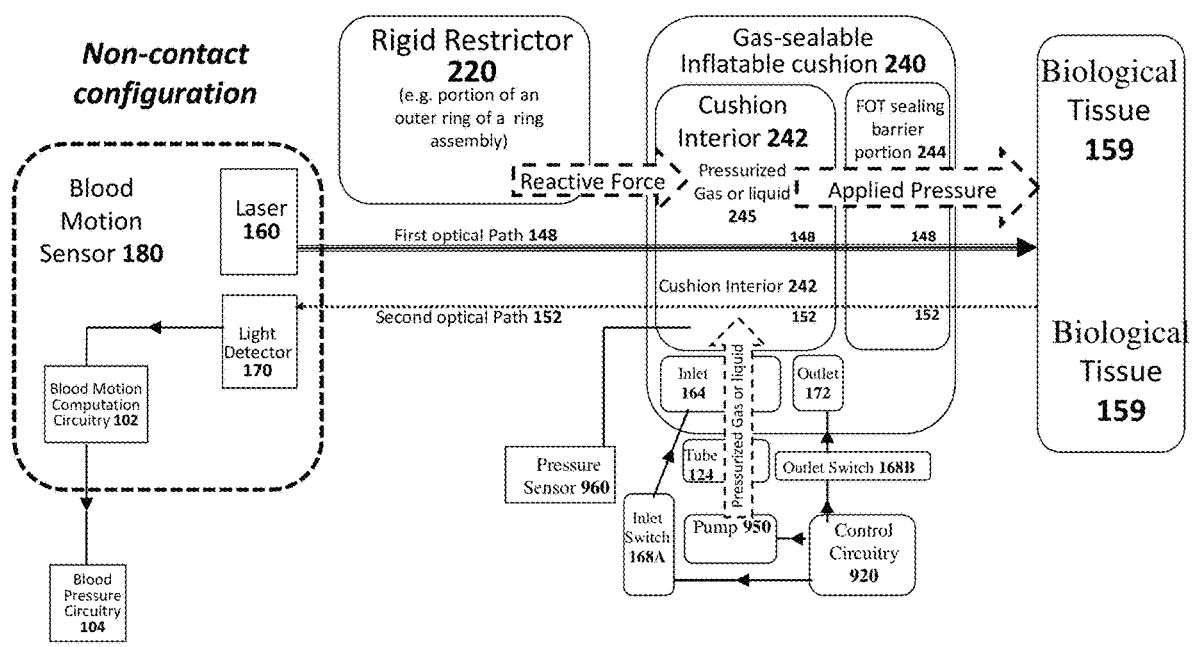
Figure 11B:
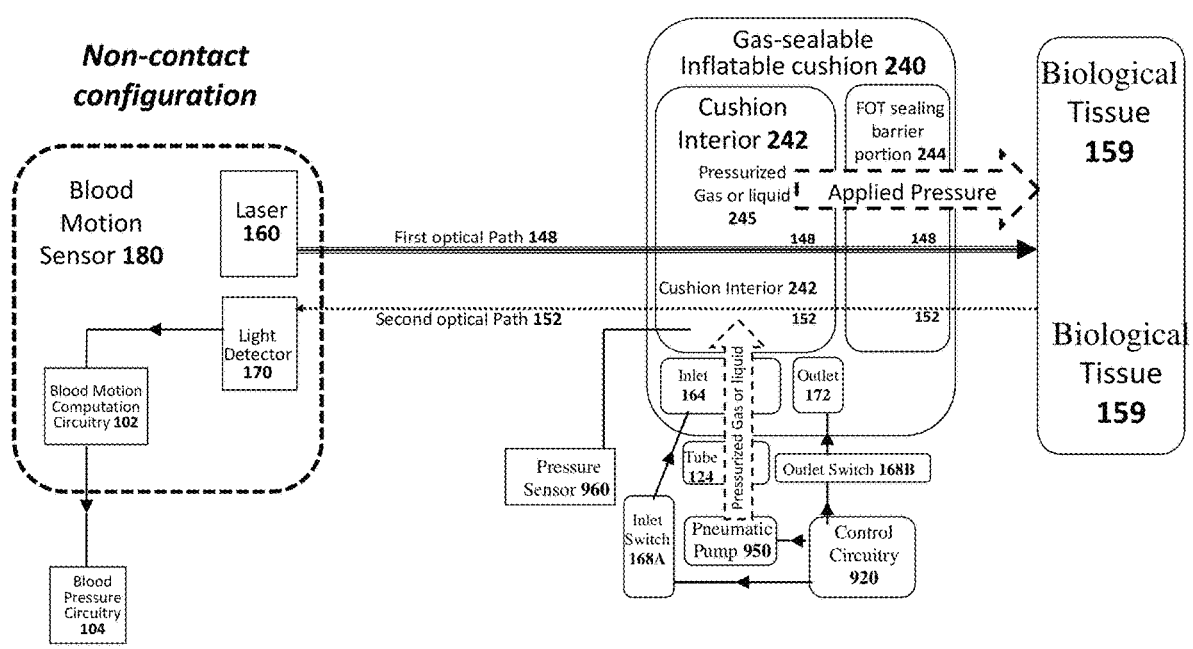

FIGS. 11A-11B illustrate alternative embodiments.

As noted above, in the example of FIGS. 3-7, 360 degrees of inner ring 104 may be a flexible (but not necessarily optically-transparent) and serve as a gas-sealing barrier of an annular shaped cushion or chamber 120. Alternatively, as shown in FIGS. 12A-12D, inner ring 104 may have the following feature—a majority but not all positions around central axis 298 (e.g. subtending $\theta_2$ as in FIG. 12B) are occupied by rigid material. Also shown in FIG. 12B is rigid insert 192 which also occupies a majority of mediating region 188 (e.g. subtending $\theta_2$ as in FIG. 12B). In the example of FIG. 12A, inward pressure is only applied at locations around central axis 298 spanning a small fraction (e.g. subtending $\theta_2$ as in FIG. 1AB) of 360 degrees. Thus may lack some of the advantages of the implementations of FIGS. 3-7 (e.g. uniform pressure around a finger or toe circumference) but, nevertheless, for various applications may be sufficient.

A Discussion of FIGS. 13-15

Systolic and/or diastolic blood pressure maybe measured during a 'ramp up' and/or 'ramp down' phase.

FIG. 13 shows two signals plotted together on the same plot—a 'pressure signal' which is the magnitude of pressure applied onto tissue 159 (i.e. including a 'ramp-up' and a 'ramp-down' phase) and blood motion signal. In one example, the systolic pressure is when the blood motion signal becomes 'pulsatile' (e.g. around 3600 in FIG. 13)

In one example, the diastolic blood pressure may be computed according to the trend line to achieve a result of around 4800 (the 'second technique'). Alternatively or additionally, diastolic blood pressure is achieved by examining a pulsatile wave form feature(s) of blood motion signal—e.g. when dichrotic notch first appears (about 4600)—see FIG. 14 for more details. Thus, for each pulsatile wave, wave form features may be analyzed—thus, as shown in FIG. 2B, blood pressure circuitry 104 may include PWF scoring engine 156.

Figure 21:
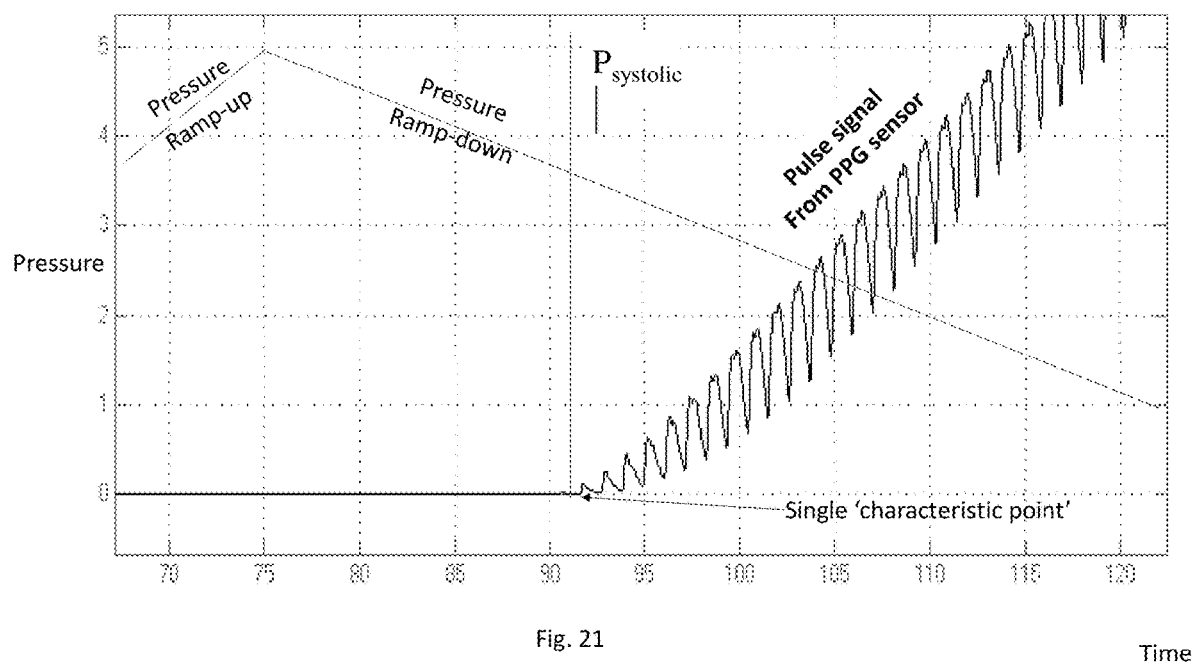
FIG. 21 illustrates a pulse signal from a PPG sensor.

The example of FIG. 13 was obtained using an optical blood pressure detection system where the blood motion sensor 180 is a DLS sensor—it is believed that similar results (i.e. for computing the diastolic blood pressure) may be obtained by employing a laser doppler sensor as blood motion sensor 180. In contrast (see FIG. 21), PPG blood motion signals (i.e. pulsatile signals) lack features for computing diastolic pulse.

Figure 15A:
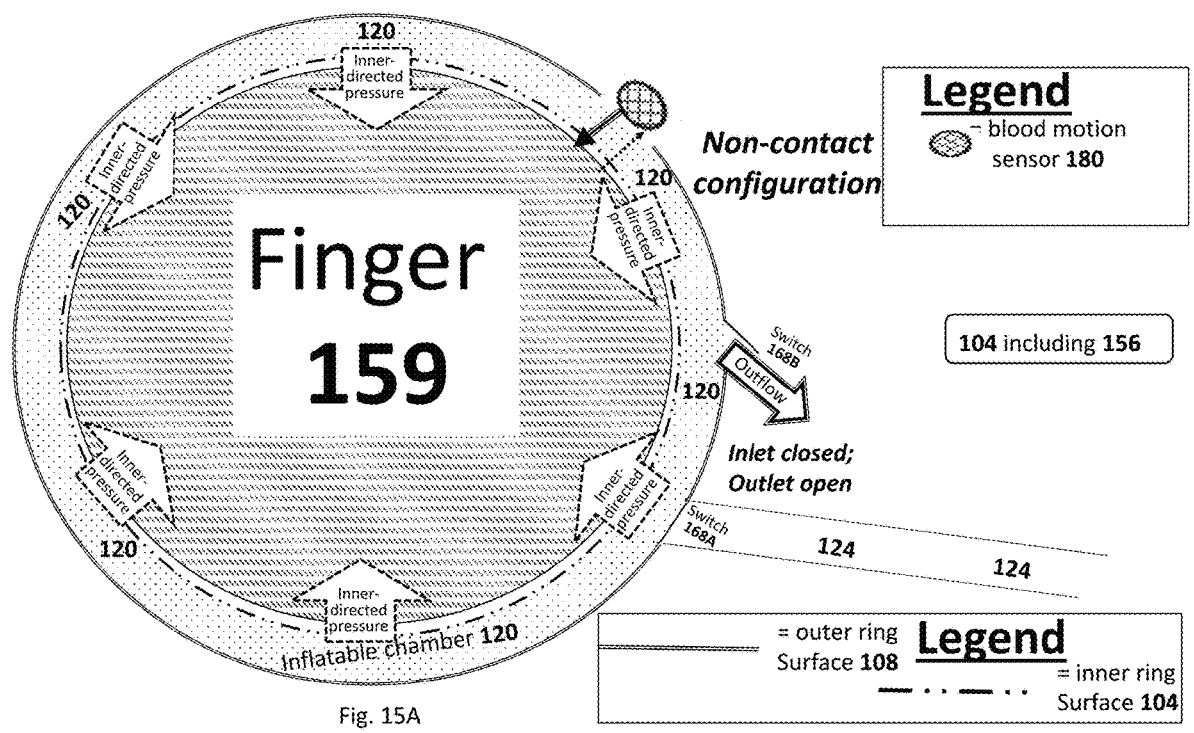
Figure 15B:
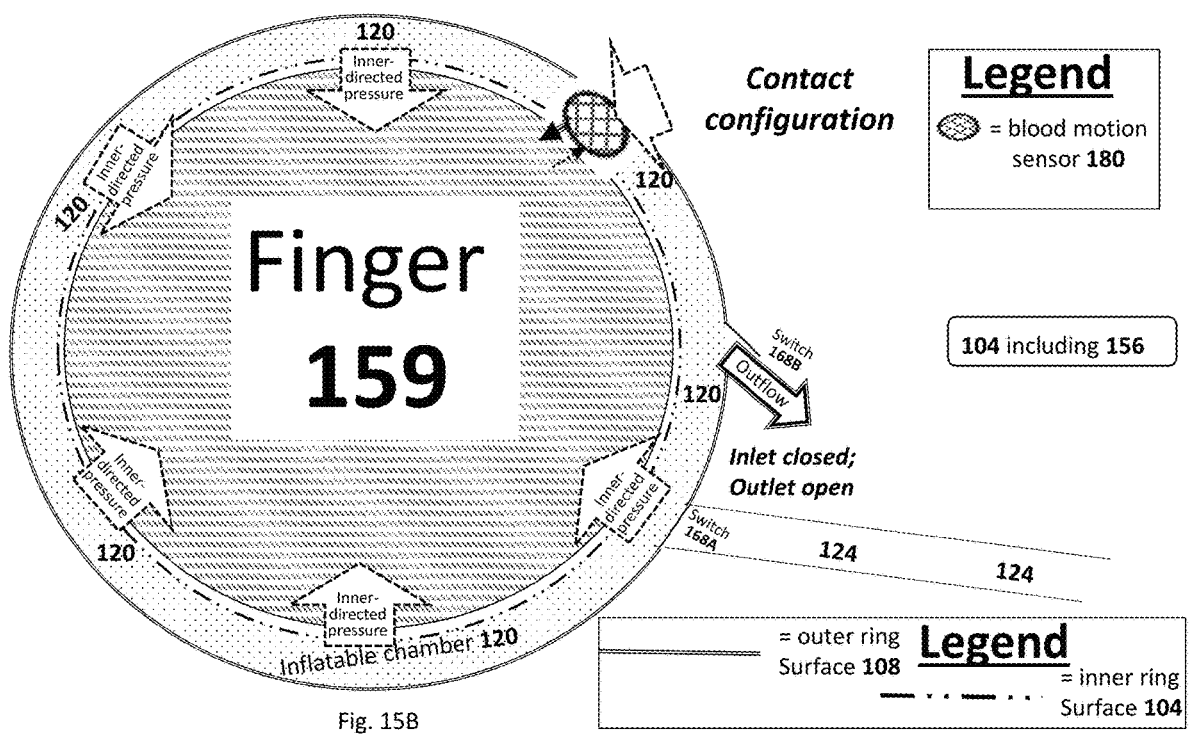
Figure 15C:
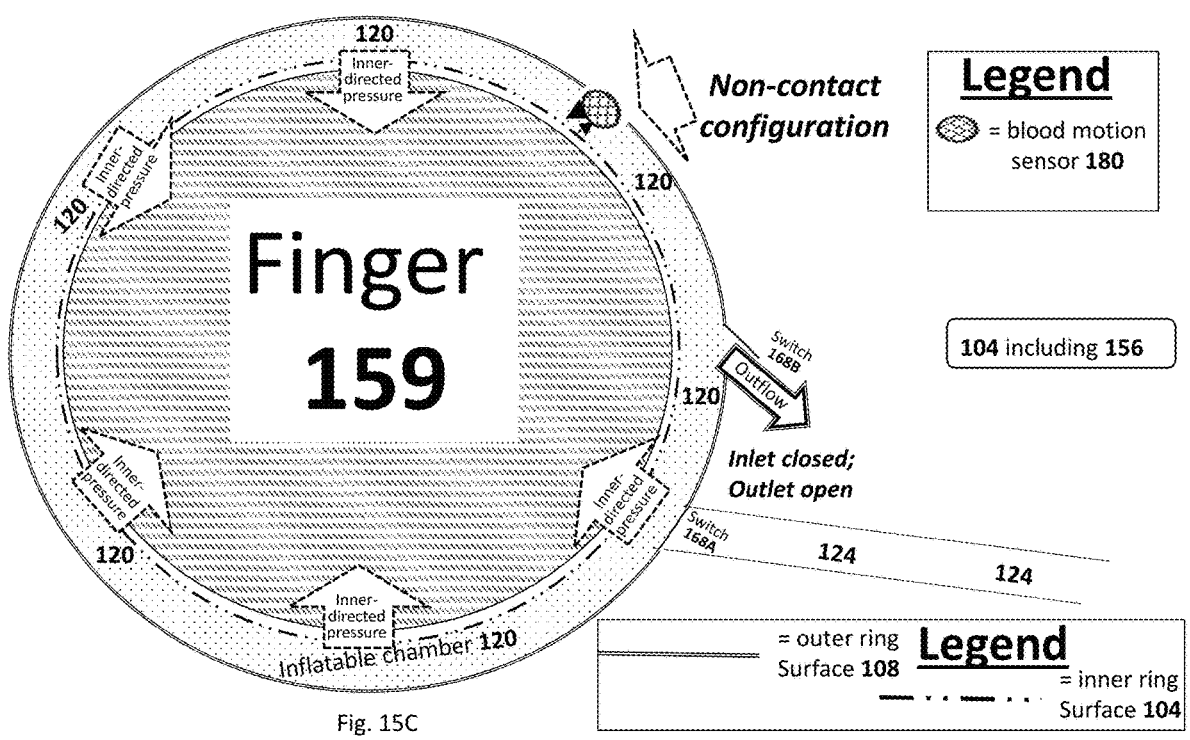

The analysis techniques of FIGS. 13-14 may be employed in systems having various mechanical and/or optical properties. Thus, FIGS. 15A and 15C show the 'non-contact configuration' e.g. to avoid mechanical interference from blood motion sensor 180. FIG. 15B shows a 'contact configuration' where such problematic mechanical interference might lead to less accurate measurements—e.g. when chamber 120 is inflated inward pressure from the inflated chamber 120 may press sensor 180 against the surface tissue 159, leading the 'mechanical interference.'

In FIG. 15C sensors 180 may be within chamber 120 or outside of chamber 120 but within ring 108.

Figure 16:
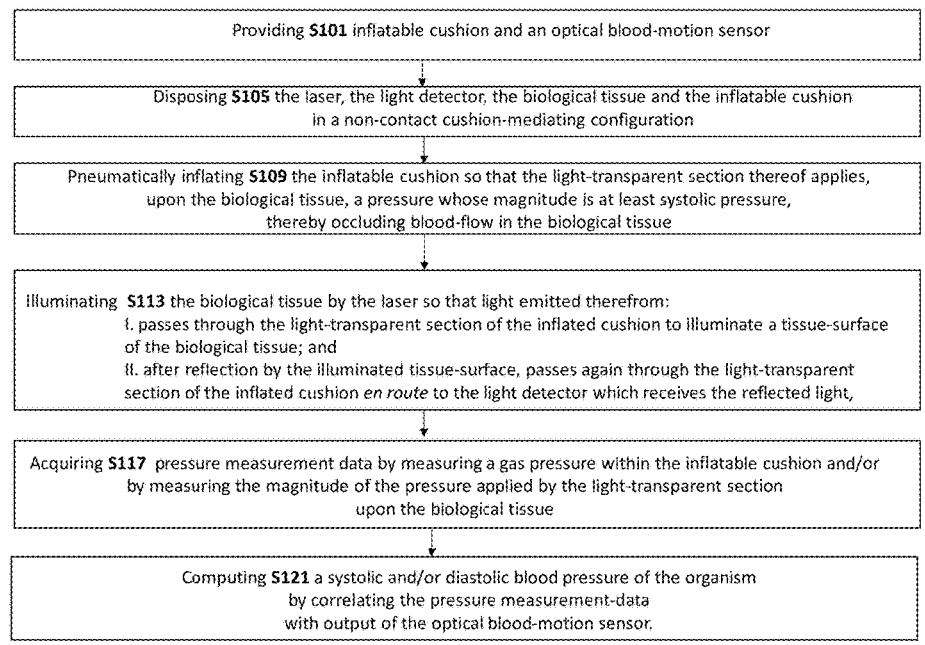

FIG. 16 including steps S101, S105, S109, S113, S117 and S121 shows another example.

A Discussion of FIGS. 17A-17D

Although some embodiments relate to a 'ring assembly' form factor, is not a limitation.

Figure 17A:
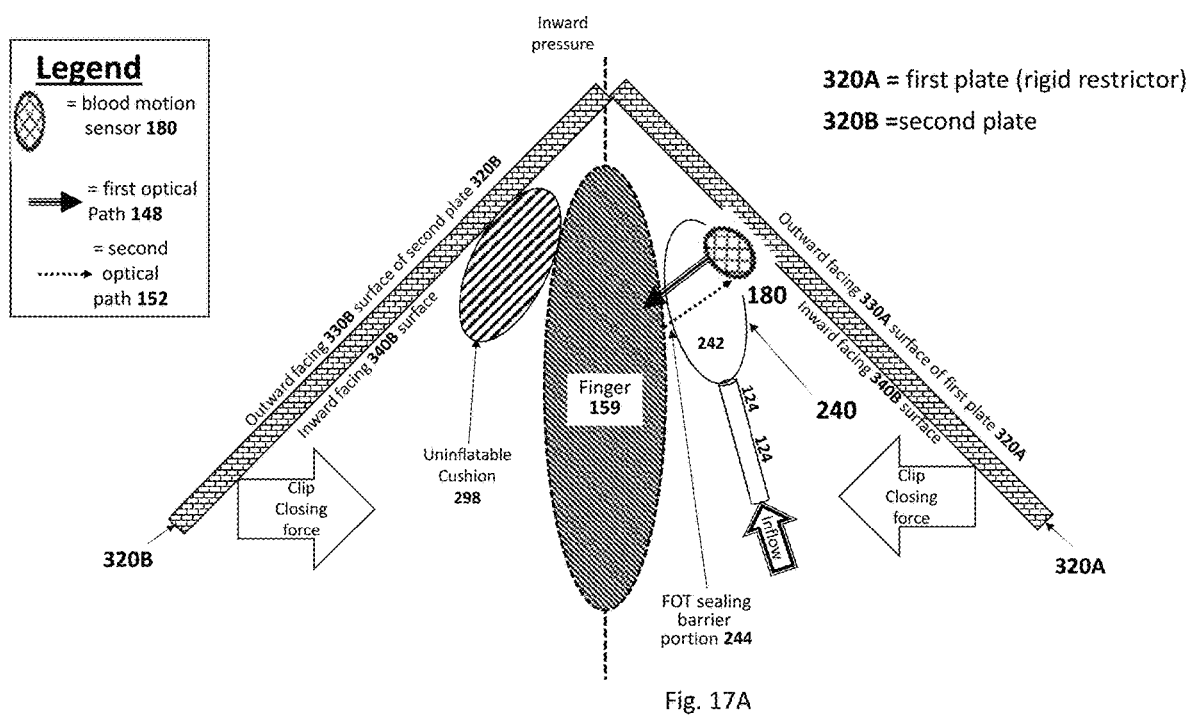
Figure 17B:
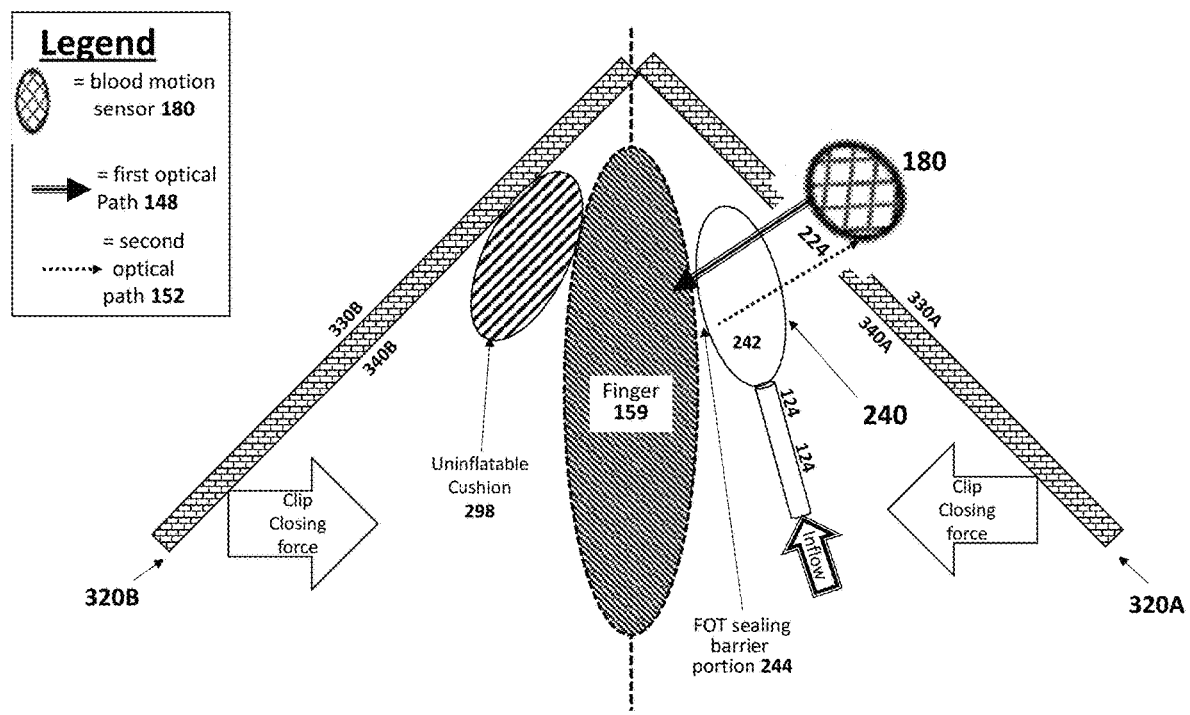
Figure 17C:
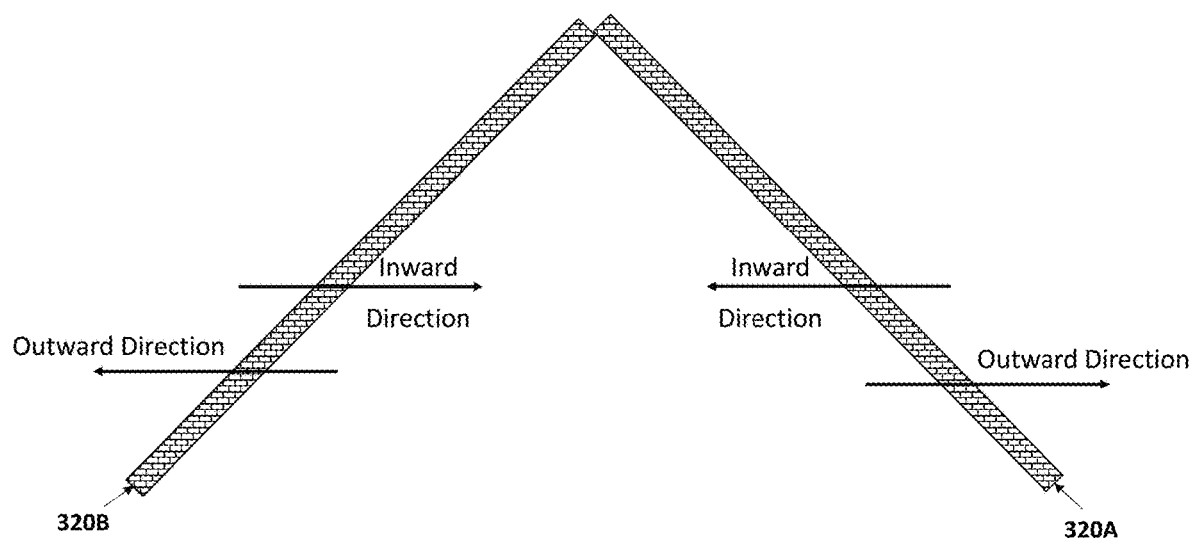
Figure 17D:
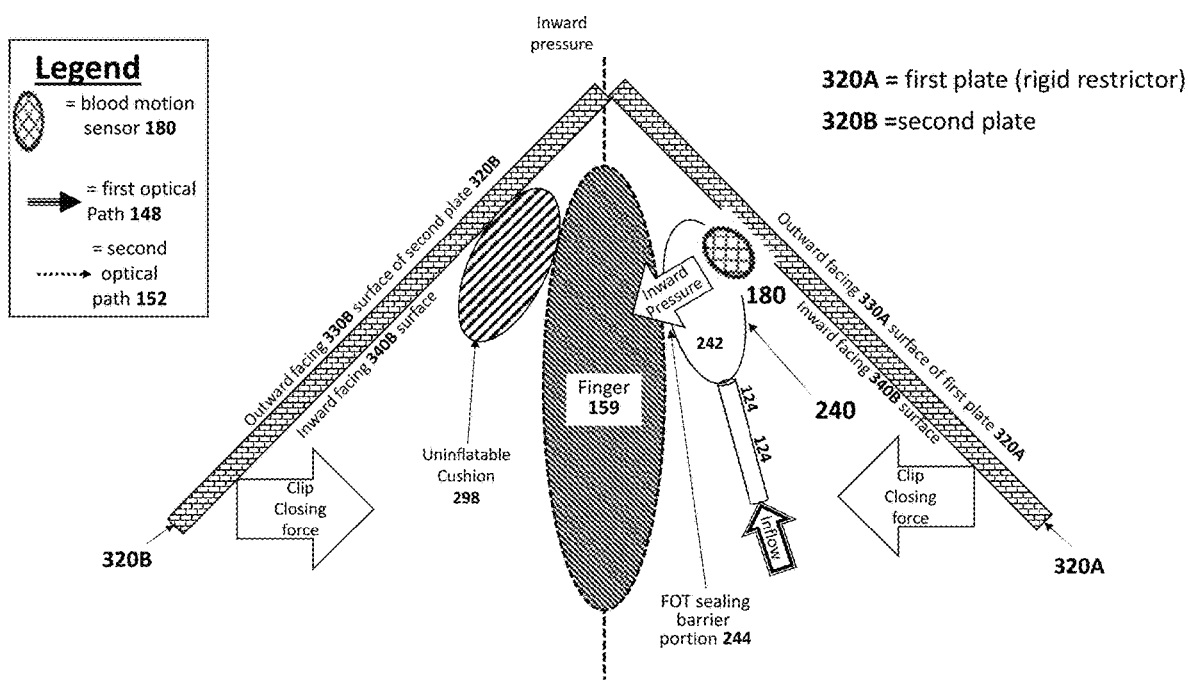

FIGS. 17A-17D relate to a 'clip form factor' device. FIG. 17C illustrates 'inward' and 'outward' directions. FIG. 17D is the same exact configuration as FIG. 17A but it shows the 'inward' 'pressure' applied (e.g. on biological tissue) by the FOT portion of the first cushion.

The clip-form-factor device for optically measuring a systolic and/or diastolic blood pressure of a mammal, the system comprising: a. first 320A and second 320B rigid plates that are connected to each other to form a V construct so that each plate is respective leg of the V construct, (e.g. the V construct being inwardly biased towards closing the V—for example, the clip-form-factor device is spring loaded), each rigid plate having inward and outward facing surfaces; b. first 240 and second 290 cushions against disposed respectively against inward-facing surfaces 340A, 340B of the first 320A and second 320B legs (e.g. and attached thereto), at least the first cushion 240 being an inflatable cushion, at least a portion 244 of a sealing barrier of the first cushion 240 being flexible and optically transparent (FOT), the first cushion 240 being mechanically coupled to the first rigid plate 320A (i.e. which functions as a restrictor 220) so that during inflation of the first cushion 220, a presence of the first plate restricts a range of motion of gas or liquid within the inflated first cushion and biases inflation-driven motion of the FOT barrier portion in an inward direction away; c. an optical blood-motion sensor comprising a laser and a light detector both of which are attached to the first rigid plate and oriented so that when the first cushion is inflated so that the FOT barrier portion applies inward pressure: A. light emitted by the laser is scattered by the pressure-applied biological tissue the pressure-applying FOT barrier portion of the inflated cushion, and the inflated cushion interior; and B. the tissue-scattered laser light is received by the light the inflated cushion interior and the optically transparent region of the rigid restrictor; iii. output of the light detector is electronically processed to compute therefrom a pressure-applied tissue blood motion signal descriptive of blood motion in the biological tissue when subjected to the applied pressure; and c. blood pressure circuitry configured to compute a systolic and/or diastolic blood pressure of the mammal by correlating a measurement of a pressure within the inflated cushion with the pressure-applied tissue blood motion signal computed by the optical blood-movement sensor.

In the example of FIG. 17A both of the laser and the light detector of the optical blood-motion sensor are disposed between the inward-facing surface of the first plate and the first cushion which is inflatable.

In the example of FIG. 17B, the first plate comprises an optically transparent region, and wherein both of the laser and the light detector of the optical blood-motion sensor are disposed on the outward-facing surface of the first plate so that when the first cushion is inflated so that the FOT barrier portion applies pressure to the biological tissue: A. light emitted by the laser is scattered by the pressure-applied biological tissue after passing through the optically transparent region of the first plate, the pressure-applying FOT barrier portion of the inflated cushion, and the inflated cushion interior; and B. the tissue-scattered laser light is received by the light detector after passing through the pressure-applying FOT barrier portion of the inflated cushion, the inflated cushion interior and the optically transparent region of the rigid restrictor.

Theoretical Discussion—Introductory Remarks

Embodiments of the invention relate to a method for measuring systolic and/or diastolic blood pressure, based on the measurement of peripheral blood flow. In some embodiments, the method is based on the speckle analysis or dynamic light scattering (DLS) technique. For example, the blood flow dynamics can be characterized in terms of the laser speckle pattern. The blood flow is described by using the laser speckle time domain parameters. This type of analysis enables to reveal different components of the flowing blood including the pulsatile and non-pulsatile.

Practically, the blood pressure $P_{pulse}$ time variation can be represented as a sum of the $P_{DC}$ (slowly fluctuating in time) and pulsating $P_{AC}$ (fluctuating with the heart rate) components. According to this representation, and taking into account Poiseuille's law, blood flow F also will consist of two parts—the one that fluctuates very slowly (DC) and pulsating component (AC).

The magnitude of AC flow, as it can be represented by DLS technique, follows the shape of the pulse wave. The magnitude of DC flow is defined by the vascular hydrodynamic resistance or impedance. This impedance is dependent also on the activation of the Micsoscopic Venous Valves (MVV). Their MVVs prevent blood reflux in small sized veins and restrict flow from post capillary venules back into the capillary bed FIG. 18 shows a simplified diagram of a fragment of vascular bed (finger) and its electric counterpart.

These valves are opened only when pressure from the artery side of vascular bed is higher, then at the vein side. Similarly, the diode will be opened only if the voltage at the anode above the cathode voltage, i.e. in the case when blocking voltage is negative. By applying external pressure by means of air cuff, the outflow of blood from the veins is prevented. Veins begin to swell and the pressure in the veins begins to rise. Static condition is achieved when the venous pressure becomes equal to the external pressure (zero transmural pressure). However, until $P_{cuff} < P_{diast}$ blood flow does not cease. After reaching condition $P_{diast} < P_{cuff} < P_{syst}$ the blood flow is interrupting only in those moments, when $P_{pulse} < P_{diast}$ (FIG. 19).

Figure 20:
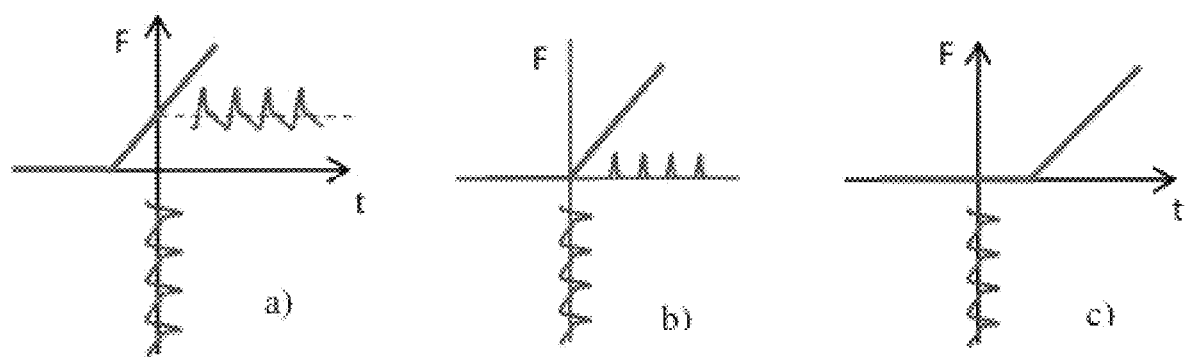

Under these conditions the AC component of the pulse wave is transformed nonlinearly, FIG. 20 shows how the pulse wave transformed by the transfer function F (P) of the venous valves in the 3 regions: a) $P_{pulse} < P_{diast}$, b) $P_{diast} < P_{cuff} < P_{sist}$, and c) $P_{cuff} > P_{sist}$.

Thus, by changing the external pressure and by measuring the blood flow response, one can find a point of diastolic pressure. If the cuff pressure is increased, the time, during which the valve is open, from the moment when $P > P_{diast}$, will start to decrease. In terms of the electrical analogy, it may be said that the conduction angle (the part of the cycle during which the diode is conducting) of the diode will start to decrease. While the pressures becomes higher then systolic $P > P_{sist}$ is detected on the base of the flow cessation and loss of pulse signal (conduction angle becomes zero).

If the measurement is made by gradually reducing the pressure (best scenario), we first define the systolic point (when the pulsating flow component appears). With further pressure decrease, we find the diastolic point, basing on the appearance of none-pulsating DC blood stream component.

So, according to some embodiments of the invention, it is possible to quantify the diastolic pressure value based on the appearance of DC blood flow component.

Theoretical Discussion About Why No Contact is Required

Embodiments of the present invention relate to systems where photodetector(s) receive light reflected from the subject's tissue. For the present disclosure 'tissue' refers to at least skin and optionally at least some additional tissue beneath the skin. The reflected light may include diffusive reflected-light (i.e. scattered light—e.g. scattered off of red blood cells within blood vessels of the subject's tissue) and/or specular reflected light. Not wishing to be bound by theory, it is noted that in contrast to PPG-based systems where a presence a significant specular reflections would destroy any functionality, the presently-disclosed DLS-based methods and apparatus may be more robust. Thus, in some embodiments, at least 10% or at least 25% or at least 50% by power of light (i.e. at the wavelength of the light source) received by each photodetector is specular-reflected light (as opposed to scattered light). The electrical signal generated by each photodetector is processed to compute therefrom the systolic and/or diastolic blood pressures.

Not wishing to be bound by theory, it is noted that specular-reflected light signal is typically characterized by a DC signal or is dominated by low frequencies signal. In contrast, the presently-disclosed DLS-based techniques (in some embodiments thereof) relies on processing the scattered-light-laser speckle optical-response descriptive electrical signal to compute therefrom the BSRD signal, which is then analyzed to compute the systolic and/or diastolic blood pressure. The BSRD is derived primarily from relatively high frequencies within the scattered-light-laser speckle optical-response descriptive electrical signal—as such, a presence of specular reflection within the optical response signal from the tissue (and within the electrical representation thereof—the scattered-light-laser speckle optical-response descriptive electrical signal) should not significantly reduce the accuracy of the computed hemodynamic information.

In embodiments of the invention, DLS may provide the following feature. This feature is its ability to measure the pulse wave at any location in the body, including the finger root or fingertip. Neither oscillometric nor auscultatory methods provide a significant signal at the finger site. The commonly used optical PPG method can be applied at the finger base or finger tip as well, but it is not related to the Korotkoff sounds, it is not accurate, and is not applicable for the assessment of diastolic pressure.

In the disclosure, unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended.

While this disclosure has been described in terms of certain embodiments and generally associated methods, alterations and permutations of the embodiments and methods will be apparent to those skilled in the art.

What is claimed is:

1. A method of optically measuring blood pressure of a mammal, the method comprising:
   a. providing a ring assembly comprising nested outer and inner rings disposed around a central axis, the inner ring comprising a section that is flexible and optically-transparent (FOT), the outer ring comprising a rigid section, the outer and inner rings defining the following three regions:
      i. an innermost region within the inside of the inner ring;
      ii. an annular-shaped mediating region outside of the inner ring and within the outer ring;
      iii. an outermost region exterior to the outer ring,
      an interior of a gas-sealable inflatable chamber being disposed in the mediating region between the FOT section of the inner ring and the rigid section of the outer ring;
   b. providing a laser and a light detector that are disposed next to each other and on the same side as the inner ring;
   c. when biological tissue of the mammal is disposed in the innermost region, inflating the chamber so as to force the FOT section of the inner ring to apply an inwardly-directed pressure upon the innermost-region-disposed biological tissue;
   d. when the cushion is inflated so that the FOT section of the inner ring applies inward pressure to the biological tissue, operating the laser and the light detector so that:
      i. light emitted by the laser is scattered and reflected by the innermost-region-disposed biological tissue after traversing both the interior of the gas-sealable inflatable chamber and the FOT section of the inner ring;
      ii. the tissue-scattered and tissue-reflected laser light is received by the light detector after traversing both the FOT section of the inner ring and the interior of the gas-sealable inflatable chamber;
   e. electronically processing output of the light detector to compute therefrom a pressure-applied tissue blood motion signal descriptive of blood motion in the biological tissue when subjected to the inwardly-directed pressure; and
   f. computing at least one of a systolic blood pressure and a diastolic blood pressure of the mammal by correlating a measurement of a pressure within the inflatable chamber with the computed pressure-applied tissue blood motion signal.

2. The method of claim 1 wherein the rigid section of the outer ring comprises an optically transparent region therein through which the laser light emitted by the laser passes through before passing traversing both the interior of the gas-sealable inflatable chamber and the FOT section of the inner ring en route to the biological tissue.

3. The method of claim 2 wherein after traversing both the FOT section of the inner ring and the interior of the gas-sealable inflatable chamber, the tissue-scattered laser light passes through the optically transparent region of the rigid section of the outer ring en route to the light detector.

4. The method of claim 1 wherein an inner surface of the outer ring is not in fluid communication with an interior of the gas-sealable chamber whose inflation drives pressure upon the biological tissue by the FOT section of the inner ring.

5. The method of any of claim 1 wherein the FOT section of the inner ring is part of a larger barrier around an interior of the gas-sealable chamber, and wherein at least one of the following is true: (i) an entirety of the larger barrier is not optically transparent; and (ii) an entirety of the larger barrier is not flexible.

6. The method of claim 1 wherein the laser, the light-sensor and the electronic circuitry are part of a laser Doppler sensor.

7. The method of claim 1 wherein the blood motion signal is a blood-shear-rate-descriptive (BSRD) signal.

8. A method for optically measuring at least one of a systolic and a diastolic blood pressure of a mammal, the method comprising:
   a. providing a rigid restrictor defining an optically transparent region therein, and an inflatable cushion, at least a portion of a sealing barrier of the inflatable cushion being flexible and optically transparent (FOT);
   b. forcing the FOT to apply pressure to the biological tissue of the mammal by inflating the inflatable cushion so that during inflation of the cushion, a presence of the rigid restrictor restricts a range of motion of gas or liquid within the inflated cushion and biases inflation-driven motion of the FOT barrier portion in a direction away from the rigid restrictor;
   c. when the cushion is inflated so that the FOT barrier portion applies pressure to the biological tissue, operating a laser and a light detector so that:
      A. light emitted by the laser is scattered and reflected by the pressure-applied biological tissue after passing through the optically transparent region of the rigid restrictor, the pressure-applying FOT barrier portion of the inflated cushion, and the inflated cushion interior; and
      B. the tissue-scattered and tissue-reflected laser light is received by the light detector after passing through the pressure-applying FOT barrier portion of the inflated cushion, the inflated cushion interior and the optically transparent region of the rigid restrictor;
   d. electronically processing output of the light detector to compute therefrom a pressure-applied tissue blood motion signal descriptive of blood motion in the biological tissue when subjected to the applied pressure; and
   e. computing at least one of a systolic blood pressure and a diastolic blood pressure of the mammal by correlating a measurement of a pressure within the inflated cushion with the computed pressure-applied tissue blood motion signal.

9. The method of claim 8 wherein:
   the rigid restrictor has first and second sides that face away from each other;
   the laser and the light detector are disposed on a first side of the rigid restrictor; and
   the cushion interior is disposed on the second side thereof.

10. The method of claim 8 wherein at least a portion of the cushion is formed by the rigid restrictor.

11. The method of claim 8 wherein the cushion interior is gas-sealed from the rigid restrictor.

12. The method of claim 8 wherein the laser, the light-sensor and the electronic circuitry are part of a laser Doppler sensor.

13. The method of claim 8 wherein the blood motion signal is a blood-shear-rate-descriptive (BSRD) signal.

14. A clip-form-factor device for optically measuring at least one of systolic and diastolic blood pressure of a mammal, the system comprising:
   a. first and second rigid plates that are connected to each other to form a V construct so that each plate is respective leg of the V construct, each rigid plate having inward and outward facing surfaces;
   b. first and second cushions against disposed respectively against inward-facing surfaces of the first and second legs, at least the first cushion being an inflatable cushion, at least a portion of a sealing barrier of the first cushion being flexible and optically transparent (FOT), the first cushion being mechanically coupled to the first rigid plate so that during inflation of the first cushion, a presence of the first plate restricts a range of motion of gas or liquid within the inflated first cushion and biases inflation-driven motion of the FOT barrier portion in an inward direction away;
   c. an optical blood-motion sensor comprising a laser and a light detector both of which are
   attached to the first rigid plate and oriented so that when the first cushion is inflated so that the FOT barrier portion applies inward pressure:
      A. light emitted by the laser is scattered by the pressure-applied biological tissue after passing through the pressure-applying FOT barrier portion of the inflated cushion and the inflated cushion interior; and
      B. the tissue-scattered laser light is received by the light detector after passing through the pressure-applying FOT barrier portion of the inflated cushion, and the inflated cushion interior;
      iii. output of the light detector is electronically processed to compute therefrom a pressure-applied tissue blood motion signal descriptive of blood motion in the biological tissue when subjected to the applied pressure; and
   c. blood pressure circuitry configured to compute at least one of a systolic blood pressure and a diastolic blood pressure of the mammal by correlating a measurement of a pressure within the inflated cushion with the pressure-applied tissue blood motion signal computed by the optical blood-movement sensor.

15. The clip-form-factor device of claim 14 wherein both of the laser and the light detector of the optical blood-motion sensor are disposed between the inward-facing surface of the first plate and the first cushion which is inflatable.

16. The clip-form-factor device of claim 14 wherein the first plate comprises an optically transparent region, and wherein both of the laser and the light detector of the optical blood-motion sensor are disposed on the outward-facing surface of the first plate so that when the first cushion is inflated so that the FOT barrier portion applies pressure to the biological tissue:
   A. light emitted by the laser is scattered by the pressure-applied biological tissue after passing through the optically transparent region of the first plate, the pressure-applying FOT barrier portion of the inflated cushion, and the inflated cushion interior; and
   B. the tissue-scattered laser light is received by the light detector after passing through the pressure-applying FOT barrier portion of the inflated cushion, the inflated cushion interior and the optically transparent region of the first plate.

17. The device of any of claim 14 wherein the V construct being inwardly biased towards closing the V.

18. The device of claim 14 wherein the optical blood-motion sensor is a laser Doppler sensor.

19. The device of claim 14 wherein the blood motion signal is a blood-shear-rate-descriptive (BSRD) signal.

20. The device of claim 14 wherein the laser and a light detector are oriented such that the tissue-scattered laser light, which is received by the light detector, is both reflected by and scattered by the pressure-applied biological tissue before the receipt by the light detector.

* * * * *